United States Patent
Mukai et al.

(10) Patent No.: US 10,205,242 B2
(45) Date of Patent: *Feb. 12, 2019

(54) TERAHERTZ DEVICE AND FABRICATION METHOD OF THE SAME

(71) Applicant: ROHM CO., LTD., Kyoto (JP)

(72) Inventors: Toshikazu Mukai, Kyoto (JP); Kazuisao Tsuruda, Kyoto (JP)

(73) Assignee: ROHM CO., LTD., Kyoto (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/614,700

(22) Filed: Jun. 6, 2017

(65) Prior Publication Data

US 2017/0271774 A1   Sep. 21, 2017

Related U.S. Application Data

(63) Continuation of application No. PCT/JP2015/066892, filed on Jun. 11, 2015.

(30) Foreign Application Priority Data

Dec. 8, 2014 (JP) ................. 2014-247779

(51) Int. Cl.
*H01Q 9/16* (2006.01)
*G01N 21/35* (2014.01)
(Continued)

(52) U.S. Cl.
CPC .......... *H01Q 9/16* (2013.01); *G01N 21/3581* (2013.01); *G01R 31/2831* (2013.01);
(Continued)

(58) Field of Classification Search
CPC .. G01N 21/3581; H01Q 9/16; G01R 31/2831; G01R 31/44; G01R 31/311; G02F 2/02; G02F 1/39
See application file for complete search history.

(56) References Cited

U.S. PATENT DOCUMENTS

2009/0051452 A1   2/2009   Asada et al.
2009/0262766 A1*  10/2009  Chen ............... H03C 7/027
                                                           372/26
(Continued)

FOREIGN PATENT DOCUMENTS

JP   2007-124250 A   5/2007
JP   2012-217107 A   11/2008
(Continued)

OTHER PUBLICATIONS

T. Wei and S. Stapleton, "Equivalent circuit and capacitance of double barrier resonant tunneling diode", J. Appl. Phys. 73(2) (Jan. 1993), pp. 829-834.

(Continued)

*Primary Examiner* — Michael C Bryant
(74) *Attorney, Agent, or Firm* — Rabin & Berdo, P.C.

(57) ABSTRACT

THz device includes: a semiconductor substrate; a first semiconductor layer disposed on the semiconductor substrate; an active element formed by being laminated on the first semiconductor layer; a second electrode connected to the first semiconductor layer to be connected to a cathode K of the active element, the second electrode disposed on the semiconductor substrate; a first electrode connected to an anode A of the active element, the first electrode disposed on the semiconductor substrate to be opposite to the second electrode; a rear reflector metal layer disposed on a back side surface of the semiconductor substrate opposite to the first semiconductor layer, wherein the active element forms a resonator between the second and first electrodes, wherein electromagnetic waves are reflected on the rear reflector metal layer, and electromagnetic waves have a surface light-emission radiating pattern or surface light-receiving pattern in a vertical direction to the semiconductor substrate.

21 Claims, 14 Drawing Sheets

(51) Int. Cl.
| | |
|---|---|
| H03B 7/08 | (2006.01) |
| G01N 21/3581 | (2014.01) |
| G01R 31/28 | (2006.01) |
| G01R 31/311 | (2006.01) |
| G02F 1/39 | (2006.01) |
| G02F 2/02 | (2006.01) |
| G02F 1/35 | (2006.01) |

(52) U.S. Cl.
CPC .............. *G01R 31/311* (2013.01); *G02F 1/39* (2013.01); *G02F 2/02* (2013.01); *H03B 7/08* (2013.01); *G02F 2001/3505* (2013.01); *G02F 2203/13* (2013.01); *H03B 2200/0084* (2013.01)

(56) References Cited

U.S. PATENT DOCUMENTS

| | | | | |
|---|---|---|---|---|
| 2010/0026401 | A1* | 2/2010 | Mukai | ...................... H03B 7/08 331/107 T |
| 2011/0248724 | A1* | 10/2011 | Sekiguchi | .............. H01Q 1/248 324/633 |
| 2013/0187721 | A1 | 7/2013 | Sekiguchi et al. | |
| 2018/0066981 | A1* | 3/2018 | Mukai | ................... G01J 1/0271 |

FOREIGN PATENT DOCUMENTS

| | | |
|---|---|---|
| JP | 2009-049692 A | 3/2009 |
| JP | 2011-155433 A | 8/2011 |
| JP | 2013-168928 A | 8/2013 |

OTHER PUBLICATIONS

C. Bayram, Z. Vashaei, and M. Razeghi, "Reliability in room-temperature negative differential resistance characteristics of low-aluminum content AlGaN/GaN double-barrier resonant tunneling diodes", Appl. Phys. Lett. 97, 181109 (Nov. 2010).

Lin'an Yang, Hanbing He, Wei Mao, and Yue Hao, "Quantitative analysis of the trapping effect on terahertz AlGaN/GaN resonant tunneling diode", Appl. Phys. Lett. 99, 153501 (Oct. 2011).

Z. Suet, D. J. Paul, J. Zhang and S. G. Turner, "Si/SiGe n-type resonant tunneling diodes fabricated using in situ hydrogen cleaning", Appl. Phys. Lett. 90, 203501 (May 2007).

* cited by examiner

TERAHERTZ DEVICE AND FABRICATION METHOD OF THE SAME

CROSS REFERENCE TO RELATED APPLICATIONS

This is a continuation application (CA) of PCT Application No. PCT/JP2015/066892, filed on Jun. 11, 2015, which claims priority to Japan Patent Application No. P2014-247779 filed on Dec. 8, 2014 and is based upon and claims the benefit of priority from prior Japanese Patent Application No. P2014-247779 filed on Dec. 8, 2014 and PCT Application No. PCT/JP2015/066892, filed on Jun. 11, 2015, the entire contents of each of which are incorporated herein by reference.

FIELD

Embodiments described herein relate to a terahertz (THz) device and a fabrication method of such a THz device.

BACKGROUND

In recent years, since miniaturization of electron devices, such as a transistor, progresses, and the size thereof has nano size, a new phenomenon called a quantum effect has been observed. Then, the development which aimed at achieving of ultra high-speed devices or new functional devices is advanced using such a quantum effect. In such environment, trials to perform large capacity communication, information processing, or imaging or measurement, etc. has been performed using the frequency region which is in particular called a THz band and of which frequency is from 0.1 THz ($10^{11}$ Hz) to 10 THz. This frequency domain is undeveloped frequency region between light and electromagnetic waves, and if the device which operates with this frequency band is achieved, being used for many uses, such as measurement in various fields, such as physical characteristics, astronomy, living things, etc. the imaging, the large capacity communication and the information processing mentioned above, is expected.

As devices for oscillating high frequency electromagnetic waves of a THz frequency band, there have been known devices having a structure in which a Resonant Tunneling Diode (RTD) and a minute slot antenna is integrated. Moreover, there have been disclosed devices having a Metal Insulator Metal (MIM) structure in which metals and an insulator are layered and the insulator is inserted between the electrode metals in order to short-circuit in terms of high frequencies, at both ends of a slot antenna.

On the other hand, although Schottky barrier diodes (SBD) are well known as THz detection devices, the SBD cannot be used as a THz oscillation device.

Although the RTD can be utilized also as detection devices also as oscillation devices, a resistive element, e.g., Bi, has to be connected between an anode and a cathode in order to reduce a parasitic oscillation, if using the RTD as THz oscillation devices.

Moreover, there has been also disclosed a THz oscillation detection device with low noise into which integrated the RTD and the SBD.

SUMMARY

The embodiments provide: a THz device which has a surface light-emission radiating pattern or a surface light-receiving pattern; and a fabrication method of such a THz device.

According to one aspect of the embodiments, there is provided a terahertz device comprising: a semiconductor substrate; a first semiconductor layer disposed on the semiconductor substrate; an active element formed by being laminated on the first semiconductor layer; a second electrode connected to the first semiconductor layer so as to be connected to one side of a main electrode of the active element, the second electrode disposed on the semiconductor substrate; a first electrode connected to another side of the main electrode of the active element, the first electrode disposed on the semiconductor substrate so as to be opposite to the second electrode; and a rear reflector metal layer disposed on a back side surface of the semiconductor substrate opposite to the first semiconductor layer, wherein the active element forms a resonator between the second electrode and the first electrode, wherein electromagnetic waves are reflected on the rear reflector metal layer, and electromagnetic waves have a surface light-emission radiating pattern or surface light-receiving pattern in a vertical direction with respect to the semiconductor substrate.

According to another aspect of the embodiments, there is provided a terahertz device comprising: a semiconductor substrate; a first semiconductor layer disposed on the semiconductor substrate; a first cathode region and a second cathode region formed by patterning the first semiconductor layer; a first resonant tunneling diode of which a first cathode is connected to the first cathode region, and a first anode is connected to the second cathode region; a second resonant tunneling diode of which a second cathode is connected to the second cathode region, and a second anode is connected to the first cathode region; and a rear reflector metal layer disposed on a back side surface of the semiconductor substrate opposite to the first semiconductor layer, wherein when the first resonant tunneling diode is biased to a negative-resistance oscillation state, the second resonant tunneling diode is biased to a resistance state, wherein electromagnetic waves are reflected on the rear reflector metal layer, and electromagnetic waves have a surface light-emission radiating pattern or surface light-receiving pattern in a vertical direction with respect to the semiconductor substrate.

According to still another aspect of the embodiments, there is provided a fabrication method of a terahertz device comprising: forming a first semiconductor layer on a semiconductor substrate; patterning the first semiconductor layer so as to form a first cathode region and a second cathode region; forming a first resonant tunneling diode of which a first cathode is connected to the first cathode region and a first anode is connected to the second cathode region; forming a second resonant tunneling diode of which a second cathode is connected to the second cathode region and a second anode is connected to the first cathode region; forming a first cathode electrode on the first cathode region, the first cathode electrode commonly connected with a second anode electrode; forming a second cathode electrode on the second cathode region, the second cathode electrode commonly connected with a first anode electrode; and forming a rear reflector metal layer on a back side surface of the semiconductor substrate opposite to the first semiconductor layer.

According to the embodiments, there can be provided the THz device which has the surface light-emission radiating pattern or the surface light-receiving pattern; and the fabrication method of such a THz device.

DESCRIPTION OF EMBODIMENTS

Figure 1:
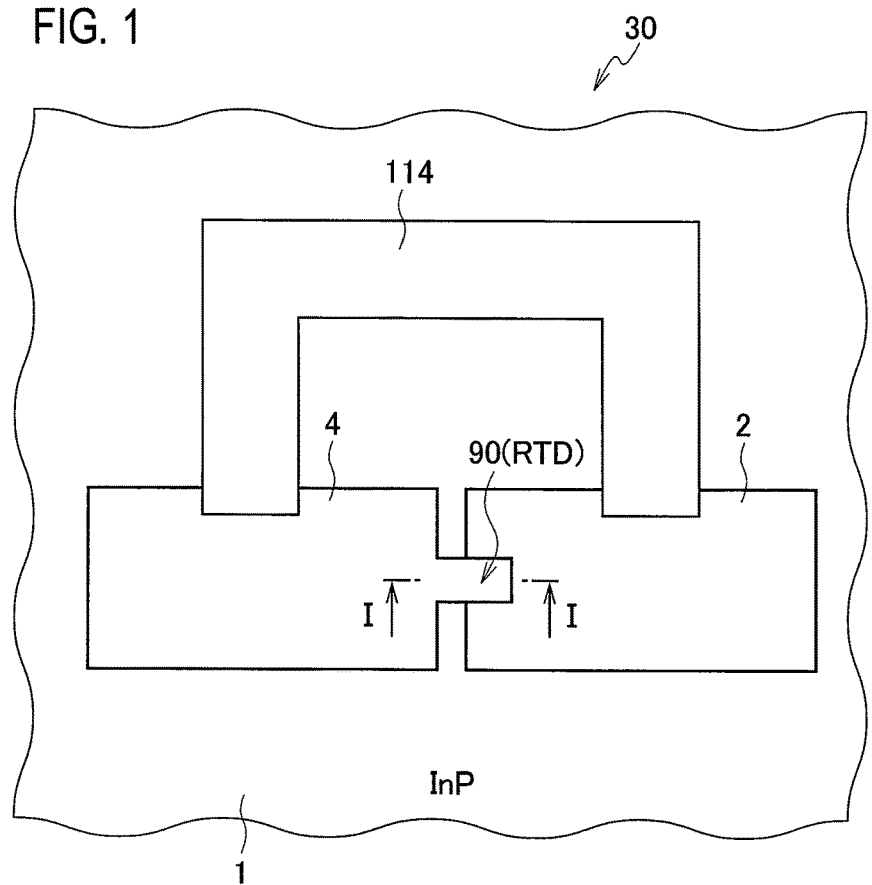
FIG. 1 is a schematic planar pattern configuration diagram showing a THz device according to the first embodiment.

Next, certain embodiments will now be described with reference to drawings. In the following drawings, same blocks or elements are designated by same reference characters to eliminate redundancy and for simplicity. However, it should be known about that the drawings are schematic and are differ from an actual thing. Of course, the part from which the relation and ratio of a mutual size differ also in mutually drawings is included.

Moreover, the embodiments shown hereinafter exemplify the apparatus and method for materializing the technical idea; and the embodiments do not intend to specify the material, shape, structure, placement, etc. of component part (s) as the following. The embodiments may be changed without departing from the spirit or scope of claims.

First Embodiment

Figure 2:
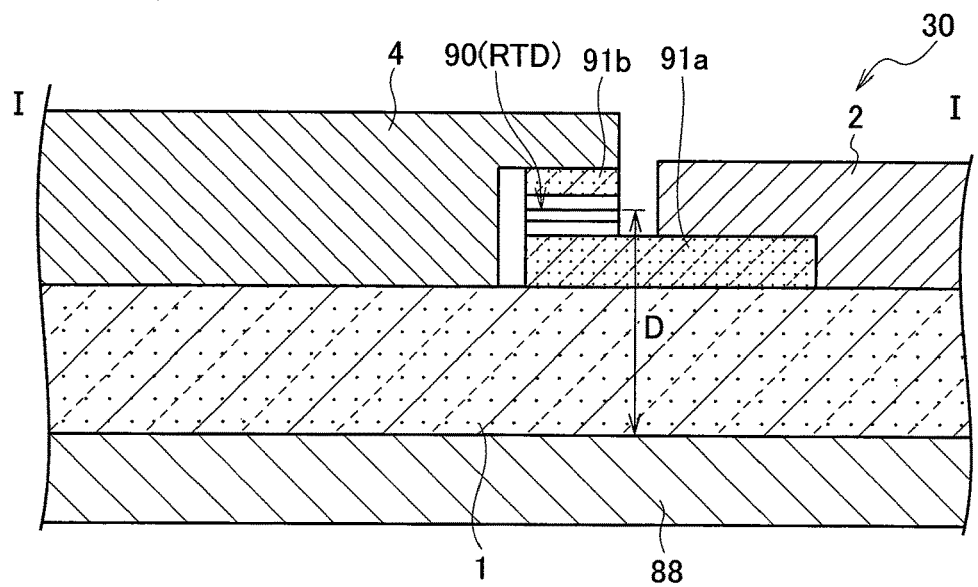
FIG. 2 is a schematic cross-sectional structure diagram taken in the line I-I of FIG. 1.

FIG. 1 shows a schematic planar pattern configuration of a THz device 30 according to the first embodiment, and FIG. 2 shows a schematic cross-sectional structure taken in the line I-I of FIG. 1.

Figure 3A:
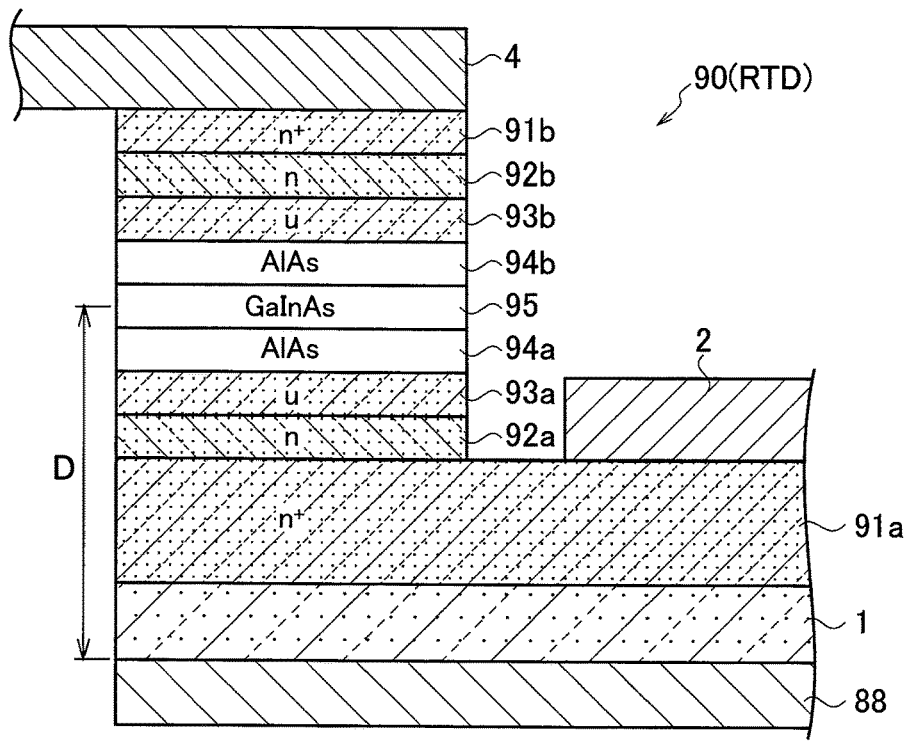
FIG. 3A is a schematic cross-sectional structure diagram showing an active element applicable to the THz device according to the first embodiment.
Figure 3B:
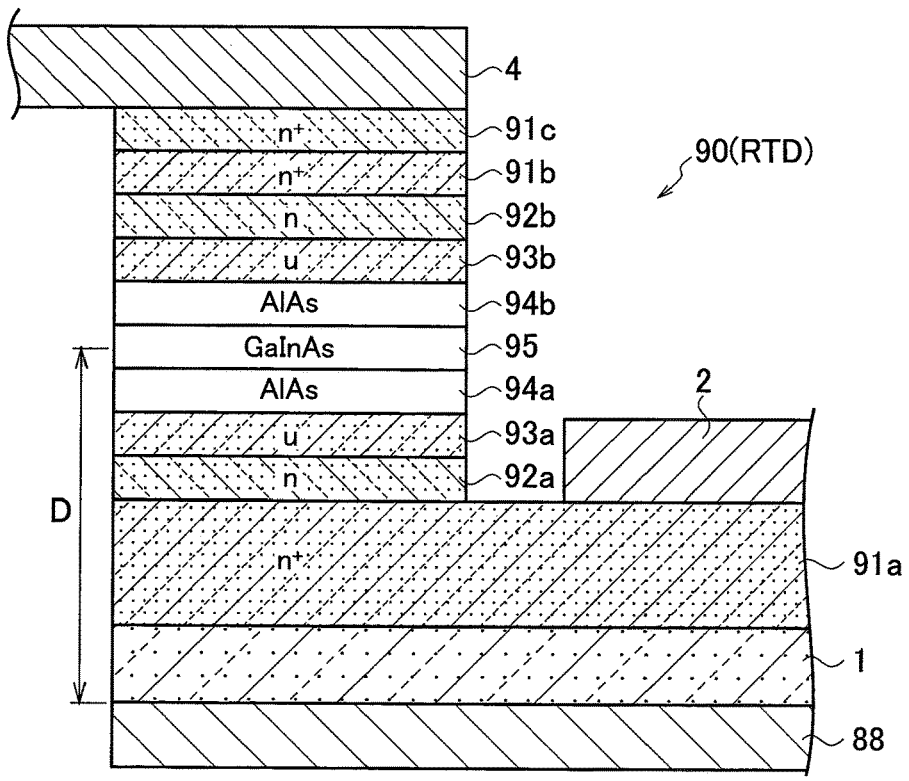
FIG. 3B is another schematic cross-sectional structure diagram showing an active element applicable to the THz device according to the first embodiment.

Moreover, FIG. 3A shows a schematic cross-sectional structure of an active element 90 applicable to the THz device 30 according to the first embodiment, and FIG. 3B shows another schematic cross-sectional structure thereof. Details of the active element 90 will be mentioned below.

(Terahertz Oscillation Device)

As shown in FIGS. 1 and 2, the THz device 30 according to the first embodiment capable of operating as a THz oscillation device includes: a semiconductor substrate 1; a first semiconductor layer 91a disposed on the semiconductor substrate 1; an active element 90 formed by being laminated on the first semiconductor layer 91a; a second electrode 2 connected to the first semiconductor layer 91a so as to be connected to one side of a main electrode of the active element 90, the second electrode 2 disposed on the semiconductor substrate 1; a first electrode 4 connected to another side of the main electrode of the active element 90, the first electrode 4 disposed on the semiconductor substrate 1 so as to be opposite to the second electrode 2; and a rear reflector metal layer 88 disposed on a back side surface of the semiconductor substrate 1 opposite to the first semiconductor layer 91a. In this case, the active element 90 forms a resonator between the second electrode 2 and the first electrode 4; and emitted electromagnetic waves are reflected on the rear reflector metal layer 88, and have a surface light-emission radiating pattern in a vertical direction with respect to the semiconductor substrate 1.

Moreover, the distance D between the active element 90 and a front side surface of the rear reflector metal layer 88 contacted with the semiconductor substrate 1 (shown in FIG. 2) is preferably ¼ times as long as an oscillation wavelength λ, in the THz device 30 according to the first embodiment. This is for the purpose of obtaining efficiently a satisfactory surface light-emission radiating pattern in the vertical direction with respect to the semiconductor substrate 1.

Moreover, as shown in FIG. 1, in the THz device 30 according to the first embodiment, the first electrode 4 and the second electrode 2 include a dipole antenna.

Figure 4:
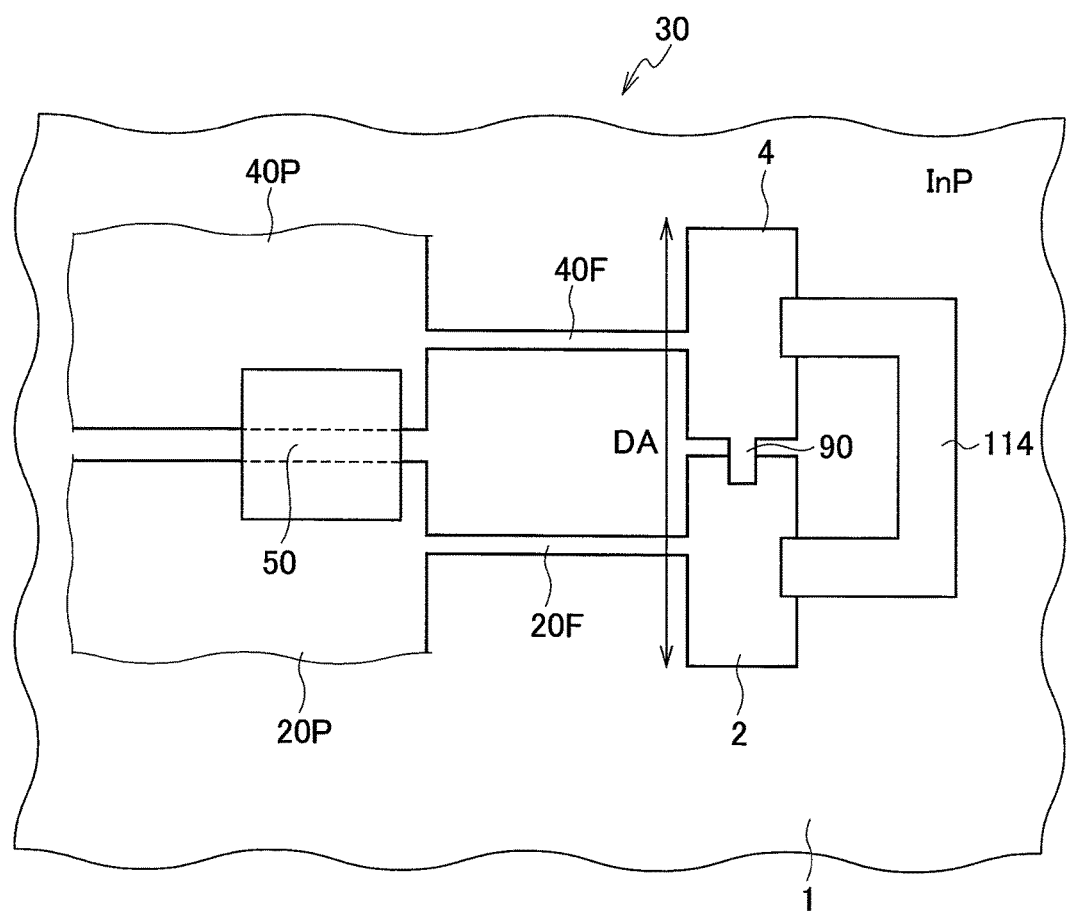
FIG. 4 is a detailed planar pattern configuration diagram showing the THz device according to the first embodiment.
Figure 5:
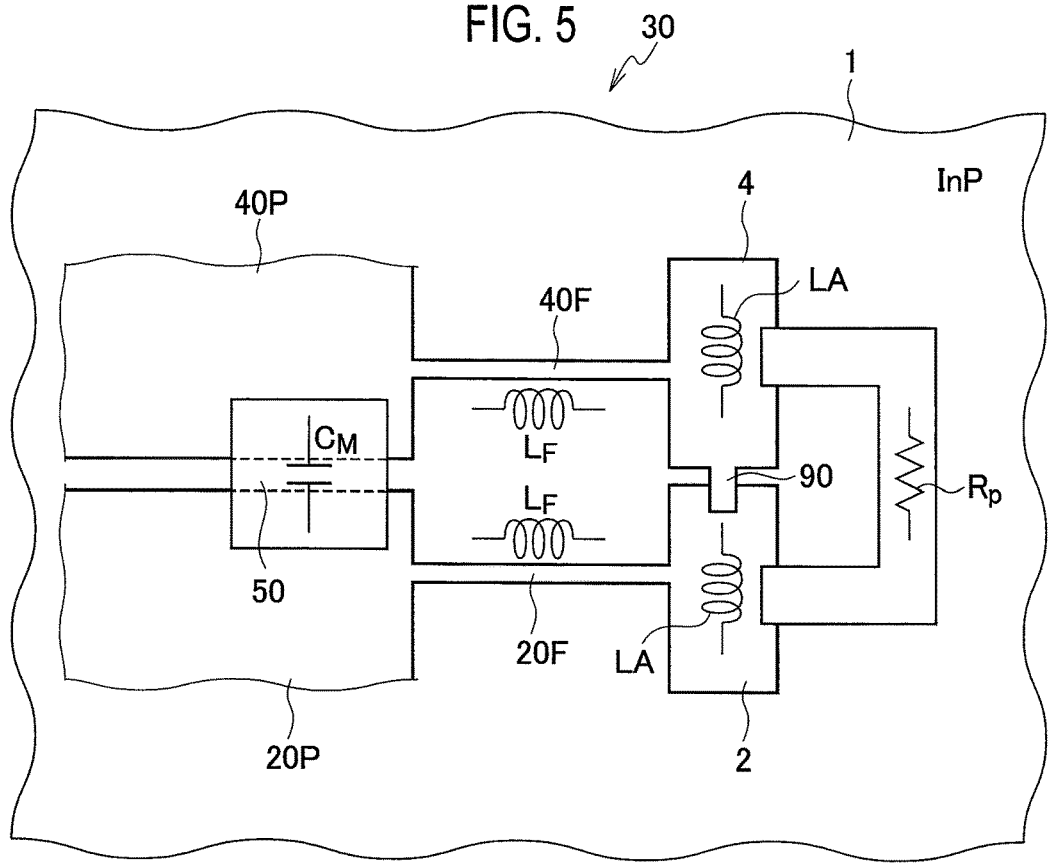
FIG. 5 is an explanatory diagram of a parasitic element parameter in FIG. 4.

FIG. 4 shows a detailed planar pattern configuration of the THz device 30 according to the first embodiment, and FIG. 5 shows an explanation of a parasitic element parameter in FIG. 4.

Figure 6:
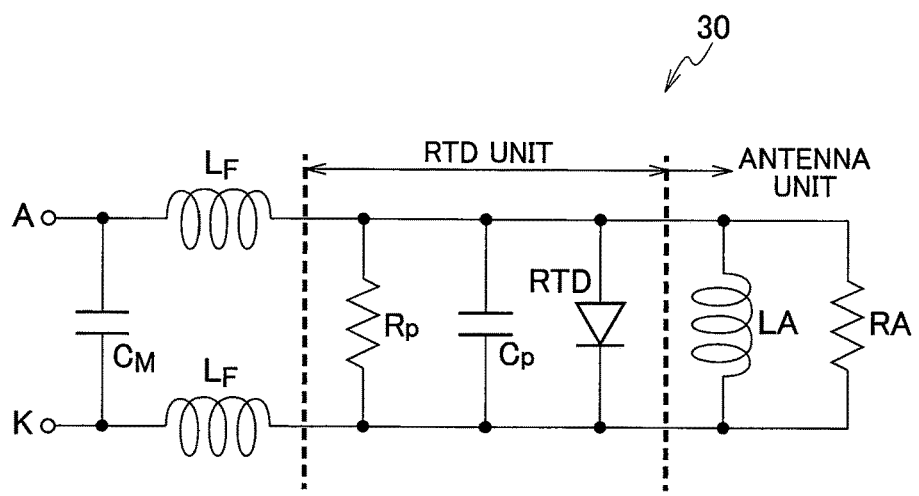
FIG. 6 is an equivalent circuit configuration diagram of the THz device according to the first embodiment.

Moreover, FIG. 6 shows an equivalent circuit configuration of the THz device 30 according to the first embodiment.

As shown in FIGS. 4 and 5, the THz device 30 according to the first embodiment may include: a first feed line 40F and a second feed line 20F each of which is connected to the dipole antenna; and a first pad electrode 40P and a second pad electrode 20P respectively connected to the first feed line 40F and the second feed line 20F.

Moreover, as shown in FIGS. 4 and 5, the THz device 30 according to the first embodiment may include an MIM reflector 50 connected between the first pad electrode 40P and the second pad electrode 20P. The MIM reflector 50 can be formed by laminating a portion of each of the pad electrodes 20P and 40P via an insulation layer.

Moreover, as shown in FIGS. 1, 4, and 5, the THz device 30 according to the first embodiment may include a resistance element 114 connected between the first electrode 4 and the second electrode 2. In the embodiment, the resistance element 114 may include metallic wiring. For example, the metallic wiring may include bismuth (Bi), nickel (Ni), titanium (Ti), or platinum (Pt).

Moreover, in the THz device 30 according to the first embodiment, the active element 90 may be arranged as multichip implementation.

Moreover, in the THz device 30 according to the first embodiment, the active element 90 may be arranged as cell array implementation.

The RTD is typical as the active element 90, but the active element 90 can be composed also from diodes or transistors except for the RTD. As other active elements, for example, a Tunnel Transit Time (TUNNETT) diode, an Impact Ionization Avalanche Transit Time (IMPATT) diode, a GaAs based Field Effect Transistor (FET), a GaN based FET, High Electron Mobility Transistor (HEMT), a Heterojunction Bipolar Transistor (HBT), etc. are also applicable thereto.

In the THz device 30 according to the first embodiment, a THz oscillation device or a THz detection device using a negative resistance of the RTD can be configured as the active element 90.

The THz device 30 according to the first embodiment includes: a first electrode 4 and a second electrode 2 configured to compose a dipole antenna unit; pad electrodes 40P and 20P configured to compose a transmission line unit; feed lines 40F and 20F configured to compose a connection unit; and a rear reflector metal layer 88 configured to form a rear reflector metal surface.

In the THz device 30 according to the first embodiment, a radiating pattern of the device can be improved, and a surface-emitting type radiating pattern can be obtained.

In the THz device 30 according to the first embodiment, if there is no metal at the back side surface thereof and the THz device 30 is mounted on a Teflon (registered trademark) substrate, for example, a radiating pattern is changed in response to an influence of a permittivity, a thickness, and an arrangement position of the Teflon (registered trademark). In the THz device 30 according to the first embodiment, the radiating pattern can be improved and the influence on the radiating pattern due to the arrangement position can also be reduced, by forming a metal surface on the back side surface of the semiconductor substrate 1.

The same effect can be produced by forming the rear reflector metal layer 88 configured to form the reflecting surface, also when operating the THz device 30 according to the first embodiment as a detection device. More specifically, the received wave pattern can be improved and the influence on the received wave pattern due to the arrangement position can also be reduced, by forming the metal surface on the back side surface of the semiconductor substrate 1.

Moreover, in the THz device 30 according to the first embodiment, change of the radiating pattern can be reduced by forming the metal on the back side surface of the device, also when sealing the device into a CAN package (metal) when putting the device to practical use.

More particularly, the first electrode 4 and the second electrode 2 may including Au/Pd/Ti or Au/Ti, for example.

Moreover, Au/Ti or Au/Pd/Ti is applicable also to the rear reflector metal layer 88, for example.

(THz Detection Device)

As shown in FIGS. 1 and 2, the THz device 30 according to the first embodiment capable of operating as a THz detection device includes: a semiconductor substrate 1; a first semiconductor layer 91a disposed on the semiconductor substrate 1; an active element 90 formed by being laminated on the first semiconductor layer 91a; a second electrode 2 connected to the first semiconductor layer 91a so as to be connected to one side of a main electrode of the active element 90, the second electrode 2 disposed on the semiconductor substrate 1; a first electrode 4 connected to another side of the main electrode of the active element 90, the first electrode 4 disposed on the semiconductor substrate 1 so as to be opposite to the second electrode 2; and a rear reflector metal layer 88 disposed on a back side surface of the semiconductor substrate 1 opposite to the first semiconductor layer 91a. In this case, the active element 90 forms a resonator between the second electrode 2 and the first electrode 4; and received electromagnetic waves are reflected on the rear reflector metal layer 88, and have a surface light-receiving pattern in a vertical direction with respect to the semiconductor substrate 1.

Moreover, the distance D between the active element 90 and a front side surface of the rear reflector metal layer 88 contacted with the semiconductor substrate 1 (shown in FIG. 2) is preferably ¼ times as long as a wavelength λ. This is for the purpose of obtaining efficiently a satisfactory surface light-receiving pattern in the vertical direction with respect to the semiconductor substrate 1. Other configuration of the THz detection device is the same as that of the THz oscillation device.

In the THz device 30 according to the first embodiment, the received wave pattern of the device can be improved and the surface receiving type received wave pattern can also be obtained.

(Parallel Resistance)

In the THz device 30 including the RTD as the active element 90, a main oscillation in THz bands is regulated due to a parasitic oscillation with respect to an external circuit resulting from the negative resistance of the RTD. As a method of suppressing the parasitic oscillation, as shown in FIGS. 1, 4, and 5, the resistance element 114 composed by including Bi is disposed in parallel to the RTD, and thereby the negative resistance can be disappeared with respect to an external circuit.

A resistance $R_{Bi}$ of the resistance element 114 is connected between the anode and the cathode of the RTD in parallel with respect to the resistance $R_{RTD}$ of the RTD. As a result, a combined resistance $R_t$ between the anode A and the cathode K of the RTD is expressed by a resistance $R_{RTD} \cdot R_{Bi}/(R_{RTD}+R_{Bi})$ by which the resistance $R_{RTD}$ of RTD is connected in parallel with the resistance $R_{Bi}$ of the resistance element 114 composed by including Bi. The resistance $R_{Bi}$ of the resistance element 114 composed by including Bi corresponds to the parallel resistance $R_p$ shown in FIG. 5.

The generation of the negative resistance ($-\Delta V/\Delta I$) is shifted to a relatively large voltage and relatively large current side by disposing the resistance $R_{Bi}$ of the resistance element 114 composed by including Bi in parallel with respect to the resistance $R_{RTD}$ of the RTD, and thereby it is effective for suppression for the parasitic oscillation.

Since the parasitic oscillation occurs in a negative resistance region between an external circuit and the THz device, the resistance is disposed in parallel to the RTD so that the negative resistance is disappeared from the external circuit. In this way, the parasitic oscillation except for the main oscillation can be suppressed.

A required condition for that purpose is expressed by the following equation from the combined resistance $R_t \geq 0$:

$$R_{Bi} <= \Delta V/\Delta I (=R_{RTD}) \quad (1)$$

By wiring with Bi having relatively high resistance value or with metals, e.g., Ni, Ti, and Pt used for semiconductor processes, the parasitic oscillation is suppressed and the main oscillation can be obtained. In the THz device 30 according to the first embodiment, the resistance wiring for suppressing the parasitic oscillation is directly connected to the dipole antenna unit.

(Equivalent Circuit Configuration)

FIG. 6 shows a simplified equivalent circuit configuration in the case of including the parallel resistance $R_p$, in the THz device 30 according to the first embodiment. In FIG. 6, reference symbols LF and LF respectively correspond to inductances of portions respectively corresponding to the feed lines 40F and 20F. Moreover, reference numeral $C_p$ denotes a parasitic capacitance of the RTD unit. Moreover, the RTD of the RTD unit is shown with the circuit symbol of diode. Moreover, the antenna unit is expressed with a parallel circuit composed by including an antenna inductance LA and an antenna resistance RA. Moreover, reference numeral $C_M$ corresponds to a capacitor of the MIM reflector 50. External circuits, e.g., a connector, a driving circuit, etc., are connected between the anode A and the cathode K.

(Parasitic Oscillation with Respect to External Circuit)

If an oscillator of THz waves is fabricated using the RTD, a parasitic oscillation occurs with respect to a portion corresponding to an external portion as circuits by being observed from the RTD. If the negative resistance of RTD is appeared from the external circuit, the Q factor in a case of oscillating with the external portion at a low frequency is higher than the Q factor of a resonant circuit which performs an RF fundamental oscillation, and thereby it becomes conditions easy to be oscillated. Accordingly, a parasitic oscillation with respect to the external circuit remarkably occurs.

(Parallel Resistance)

As a method to generally suppress the parasitic oscillation, as shown in FIGS. 1, 4, 5, and 6, the parallel resistance $R_p$ is disposed with respect to the RTD. Thereby, it is devised so that the Q factor of the parasitic oscillation is reduced to suppress the parasitic oscillation, and electric power is efficiently interchanged to the main oscillation side.

If the negative resistance is disappeared from the external by disposing the parallel resistance $R_p$, the Q factor of the parasitic oscillation which is oscillated with respect to the external at a low frequency is decreased, and the parasitic oscillation is hard to occur, compared with the RF fundamental oscillation. Accordingly, the fundamental RF fundamental oscillation occurs.

(Q Factor)

Briefly explaining the Q factor, the Q factor is an index indicating how steady the oscillation state is existing. The Q factor when the parallel resonant circuit is considered is expressed by the following equation:

$$Q = 1/R_t \cdot \sqrt{(LA/C_p)} \quad (2)$$

Such disposition of the parallel resistance $R_p$ corresponds to increasing the combined resistance $R_t$.

If the Q factor of the parasitic oscillation as expressed above is considered on the basis of the Equation (2), the disposition of the parallel resistance $R_p$ corresponds to increasing the combined resistance $R_t$, and decrease of the Q factor can be realized as a result. It is proved that the parasitic oscillation can be suppressed by disposing the parallel resistance $R_p$.

(Example of Microphotograph of Device Surface of RTD)

Figure 7:
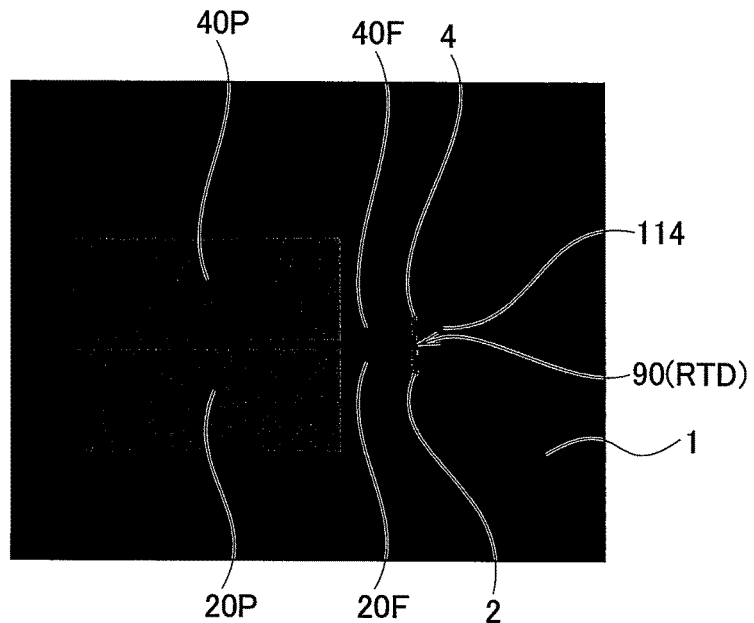
FIG. 7 shows an example of a microphotograph of a surface of the THz device according to the first embodiment.
Figure 8:
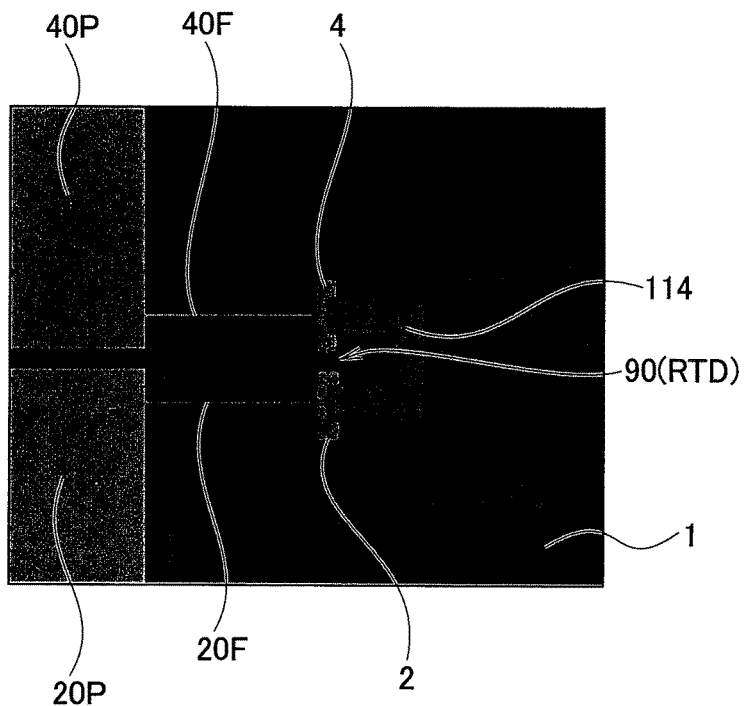
FIG. 8 shows an example of an enlarged microphotograph of the surface of the device shown in FIG. 7.

FIG. 7 shows an example of a microphotograph of a surface of the THz device 30 according to the first embodiment, and FIG. 8 shows an example of an enlarged microphotograph of the surface of the device shown in FIG. 7. The example shown in FIG. 7 and corresponds to a detailed example of a planar pattern configuration of the THz device 30 according to the first embodiment shown in FIG. 4. Although the example in which the MIM reflector 50 is not formed is shown in FIGS. 7 and 8, the MIM reflector 50 can be formed by laminating a portion of each of the pad electrodes 20P and 40P via an insulation layer in the same manner as FIG. 4.

In the THz device 30 according to the first embodiment, the parallel resistance $R_p$ can be fabricated using Bi having relatively high resistance value or metals, e.g., Ni, Ti, Pt, etc., used for semiconductor processes. A step coverage of stepped portions due to a structure of the device can be improved by oblique deposition etc., and thereby a demonstration of operation of the device can be realized.

(Oscillation Frequency Characteristics)

Figure 9:
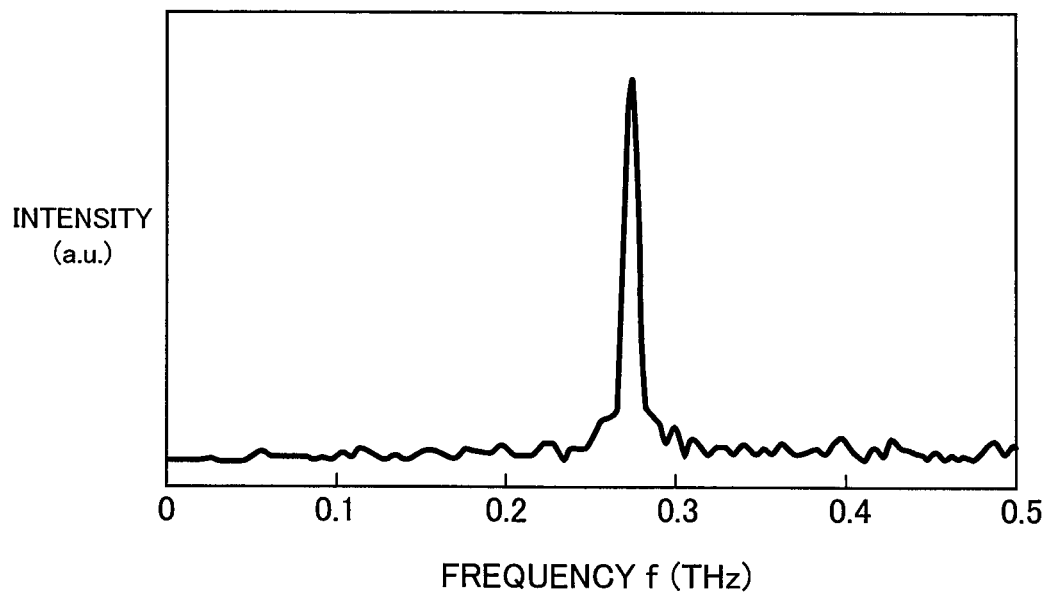
FIG. 9 shows oscillation frequency characteristics of the THz device according to the first embodiment.

FIG. 9 shows an example of oscillation frequency characteristics of the THz device 30 according to the first embodiment. In the example shown in FIG. 9, a peak of oscillation intensity (arbitrary unit) is obtained at approximately 0.27 THz.

(Simulation Result)

Figure 10A:
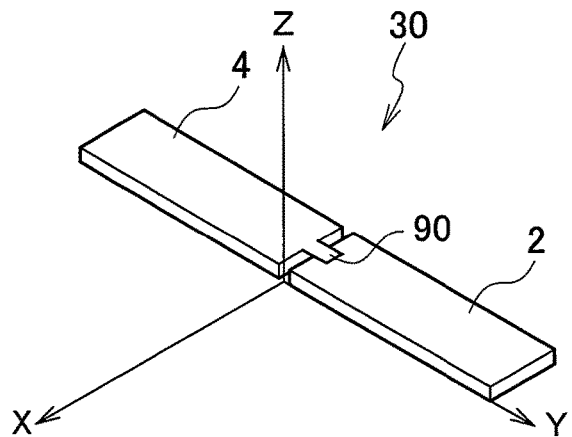
FIG. 10A is a schematic bird's-eye view of the THz device according to the first embodiment used for a dipole antenna calculation model.
Figure 10B:
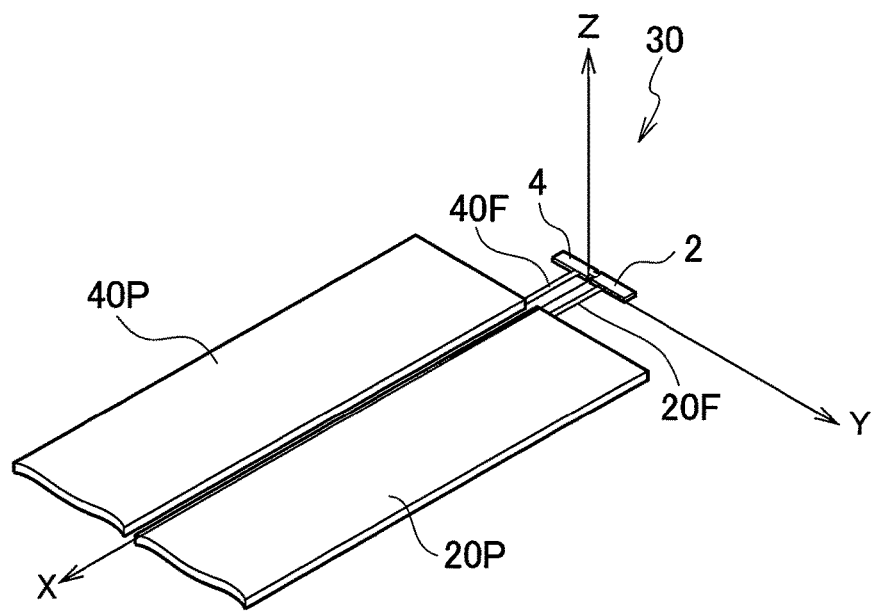
FIG. 10B is a schematic bird's-eye view of the THz device according to the first embodiment used for the dipole antenna calculation model including a feed line and a pad electrode.

FIG. 10A shows a schematic bird's-eye view of the THz device 30 according to the first embodiment used for a dipole antenna calculation model, and FIG. 10B shows a schematic bird's-eye view of the THz device 30 according to the first embodiment used for the dipole antenna calculation model including the feed lines 40F and 20F and the pad electrodes 40P and 20P. Both are calculated as the models including the rear reflector metal layer 88.

In the present embodiment, the pad electrodes 40P and 20P respectively compose transmission lines. The width of the pad electrodes 40P and 20P (width of the transmission lines) is set to 75 μm, for example, a gap between the pad electrodes 40P and 20P (gap between the transmission lines) is set to 5 μm, for example, and the length of the pad electrodes 40P and 20P (the length of the transmission lines) is set to 300 μm, for example.

The feed lines 40F and 20F compose a connection unit between the dipole antenna (2 and 4) and the pad electrodes 40P and 20P. The length of the feed lines 40F and 20F is set to a range of 20 μm to 100 μm, for example, and the width thereof is set to a range of 1 μm to 10 μm, for example.

Moreover, an antenna length DA of the dipole antenna (2, 4) (refer to FIG. 4) is set to 320 μm, for example.

Figure 11B:
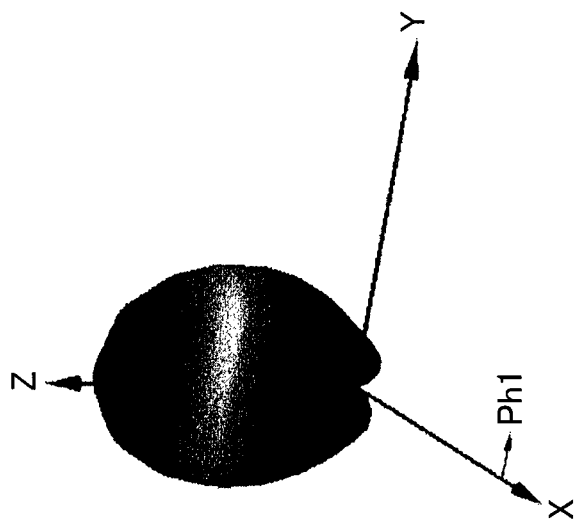
FIG. 11B shows a simulation result in an oscillation frequency of 320 GHz.
Figure 11A:
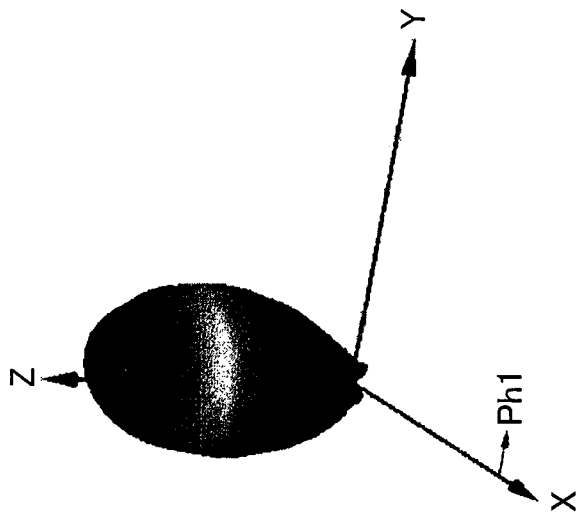
FIG. 11A is a simulation result in an oscillation frequency of 300 GHz in a radiating pattern of the THz device according to the first embodiment.

FIG. 11A shows a simulation result in an oscillation frequency of 300 GHz in a radiating pattern of the THz device 30 according to the first embodiment, and FIG. 11B shows a simulation result in an oscillation frequency of 320 GHz. The simulation results shown in FIGS. 11A and 11B are results of being calculated on the basis of the dipole antenna calculation model including the feed lines 40F and 20F and the pad electrodes 40P and 20P shown in FIG. 10B.

In the THz device 30 according to the first embodiment, a satisfactory surface-emitting type radiating pattern is obtained at equal to or less than approximately 330 GHz, for example, as clearly from the simulation results.

Compared with a chip area (1.5 mm×3.0 mm) of the THz device including a tapered slot antenna as a comparative example, a chip area of the THz device 30 according to the first embodiment including the dipole antenna is approximately 0.5 mm×0.5 mm, for example, and is microfabricated to approximately 1/18 of the chip area of the comparative example. Furthermore, the chip size thereof can also be microfabricated to equal to or less than approximately 0.5 mm×0.5 mm.

In the THz device 30 according to the first embodiment, the rear reflector metal layer 88 is disposed on the entire back surface of the semiconductor substrate 1, and thereby surface light emission radiation of the THz waves to the semiconductor substrate front surface side can be realized using reflection by the rear reflector metal layer 88. The oscillation frequency can be controlled by changing the antenna length DA. Moreover, antenna efficiency can also be controlled by adjusting the length, the width, or the arrangement position of the feed lines 40F and 20F which compose the connection unit.

—RTD—

As shown in FIG. 3A, a constructional example of the RTD as the active element 90 applicable to the THz device according to the first embodiment includes: a GaInAs layer 91a disposed on a semiconductor substrate 1 composed by including a semi insulating InP substrate, the GaInAs layer 91a highly doped with an n type impurity; a GaInAs layer 92a disposed on the GaInAs layer 91a, the GaInAs layer 92a doped with an n type impurity; a undoped GaInAs layer 93a disposed on the GaInAs layer 92a; an RTD portion composed by including an AlAs layer 94a/GaInAs layer 95/AlAs layer 94b disposed on the GaInAs layer 93a; an undoped GaInAs layer 93b disposed on the AlAs layer 94b; a GaInAs layer 92b disposed on the GaInAs layer 93a, the GaInAs layer 92b doped with an n type impurity; a GaInAs layer 91b disposed on the GaInAs layer 92b, the GaInAs layer 91b highly doped with an n type impurity; a first electrode 4 disposed on the GaInAs layer 91b; and a second electrode 2 disposed on the GaInAs layer 91a.

As shown in FIG. 3B, another configuration example of the RTD as the active element 90 applicable to the THz device 30 according to the first embodiment includes a GaInAs layer 91c disposed on the GaInAs layer 91b, the GaInAs layer 91c highly doped with an n type impurity, and the first electrode 4 is disposed on the GaInAs layer 91c. Thus, the GaInAs layer 91c may be formed in order to realize more satisfactory contact between the first electrode 4 and the GaInAs layer 91b.

In the embodiment, the thickness of each layer is, for example, as follows:

The thicknesses of the $n^+$ GaInAs layers 91a, 91b, 91c are respectively approximately 400 nm, approximately 15 nm, and approximately 8 nm, for example. The thicknesses of the n type GaInAs layers 92a and 92b are substantially equal to each other, and respectively are approximately 25 nm, for example. The thicknesses of the undoped GaInAs layers 93a and 93b are thicknesses for realizing the above-mentioned asymmetry, for example, and respectively are approximately 2 nm and 20 nm. The thicknesses of the AlAs layers 94a and 94b are equal to each other, and respectively are approximately 1.1 nm, for example. The thickness of the GaInAs layer 95 is approximately 4.5 nm, for example.

In addition, an $SiO_2$ film, an $Si_3N_4$ film, a SiON film, an $HfO_2$ film, an $Al_2O_3$ film, etc., or an insulating film composed by including the aforementioned multilayer films is deposited on the sidewall part of the layered structure shown in FIGS. 3A and 3B. The insulating layer can be formed by a CVD (Chemical Vapor Deposition) method or a spattering technique.

Due to the layered structure composed by including the metal/insulator/metal of the MIM reflector 50, the pad electrodes 40P, 20P are short-circuited in terms of high frequencies. Moreover, the MIM reflector 50 produces an effect to reflect high-frequency waves as it is open in terms of direct current.

Each of the first electrode 4 and the second electrode 2 is composed by including a metal layered structure of Au/Pd/Ti, for example, and the Ti layer is a buffer layer for making satisfactory a contact state with the semiconductor substrate 1 including a semi insulating InP substrate. The thickness of each unit of the first electrode 4 and the second electrode 2 is approximately several 100 nm, for example, and a planarized layered structure is produced as a whole. Each of the first electrode 4 and the second electrode 2 can be formed by a vacuum evaporation method or a sputtering technique.

The insulation layer of the MIM reflector can be formed including a $SiO_2$ film, for example. Other films, e.g. an $Si_3N_4$ film, a SiON film, an $HfO_2$ film, an $Al_2O_3$ film, etc. are also applicable to the insulating film. In addition, the thickness of the insulating layer can be determined in consideration of a geometric plane size of the MIM reflector 50 and a required capacitor value on circuit characteristics, for example, and may be set to several 10 nm to several 100 nm. The insulating layer can be formed by CVD or a spattering technique.

In the THz device 30 according to the first embodiment, although an example of the first tunnel barrier layer/quantum well layer/second tunnel barrier layer has a configuration of AlAs/InAlAs/AlAs is shown, it is not limited to such materials. For example, an example of the first tunnel barrier layer/quantum well layer/second tunnel barrier layer having a configuration of AlGaAs/GaAs/AlGaAs may be suitable therefor. Alternatively, an example of the first tunnel barrier layer/quantum well layer/second tunnel barrier layer having a configuration of AlGaN/GaN/AlGaN may be suitable therefor. Alternatively, an example of the first tunnel barrier layer/quantum well layer/second tunnel barrier layer having a configuration of SiGe/Si/SiGe may be suitable therefor.

According to the first embodiment, there can be provided the THz device which has the surface light-emission radiating pattern or the surface light-receiving pattern.

Second Embodiment

The THz device 30 according to the second embodiment includes a second RTD2 connected in reversely parallel to a first RTD1, instead of the resistance element 114 included in the THz device 30 according to the first embodiment.

Figure 21:
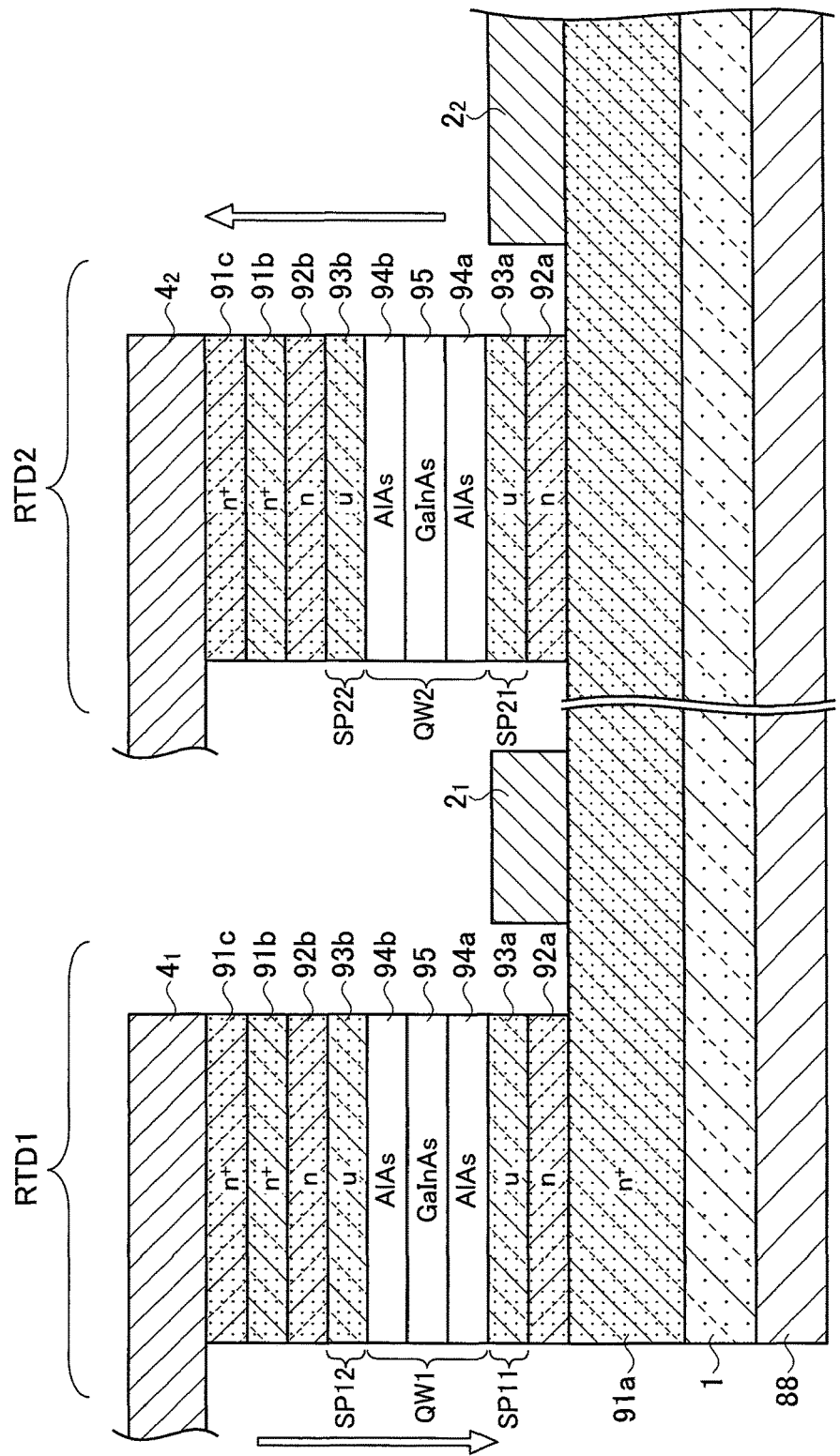
FIG. 21 is a schematic cross-sectional structure diagram which can be formed by simultaneous processes of the RTD1 and RTD2 applicable to the THz device according to the second embodiment.

FIG. 21 shows a schematic cross-sectional structure of the first RTD1 and the second RTD2 applicable to the THz device 30 according to the second embodiment. FIG. 21 shows an example of the first RTD1 and the second RTD2 being integrated onto the same semiconductor substrate 1. Alternatively, the first RTD1 and the second RTD2 respectively may be formed as different elements.

A rear reflector metal layer 88 is disposed on a back side surface of the semiconductor substrate 1 of the THz device 30 according to the second embodiment in the same manner as the THz device 30 according to the first embodiment. In FIG. 21, the direction shown by the arrow is a direction along which a forward current flows. The details of the device structure will be mentioned below.

Figure 12:
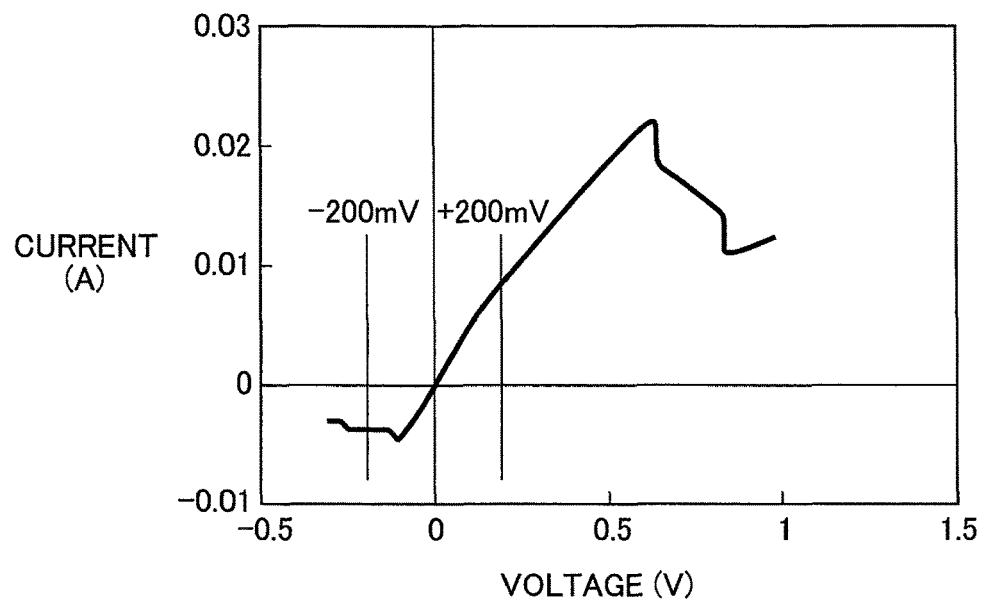
FIG. 12 shows an example of asymmetrical current-voltage characteristics of an RTD1 applicable to the THz device according to a second embodiment.

FIG. 12 shows an example of asymmetrical current-voltage characteristics of the first RTD1 applicable to the THz device 30 according to the second embodiment.

Figure 13:
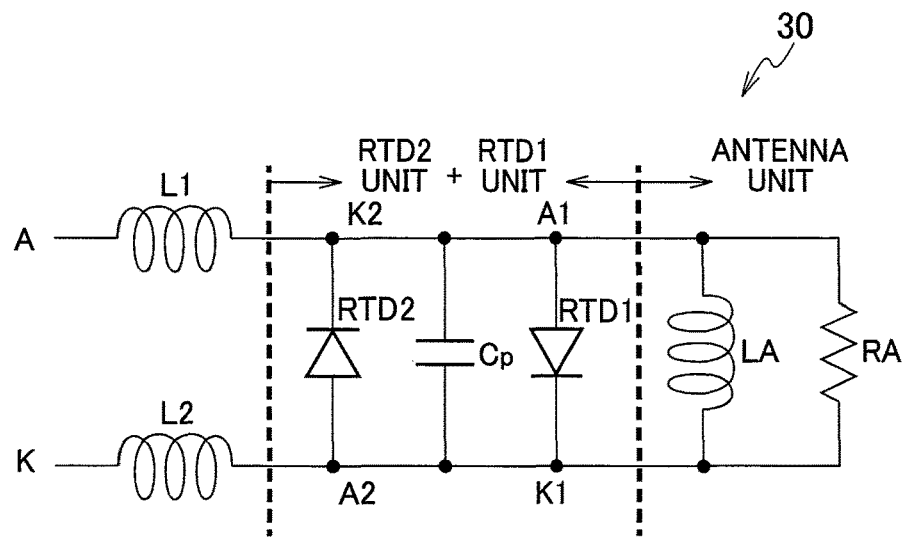
FIG. 13 is an equivalent circuit configuration diagram of the THz device according to the second embodiment.

Moreover, FIG. 13 shows an equivalent circuit configuration of the THz device 30 according to the second embodiment.

As shown in FIG. 13, the THz device 30 according to the second embodiment includes: a first RTD1 including a first anode A1 and a first cathode K1; and a second RTD2 including a second anode A2 and a second cathode K2. If the one of the first RTD1 and the second RTD2 is biased to a negative-resistance oscillation state, the other is biased to a resistance state.

For example, in FIG. 12, although it can be considered that the first RTD1 is a pure resistance if the forward voltage value is a bias state of +200 mV, it can be considered that the first RTD1 is a negative resistance state if forward voltage value is a bias state of −200 mV. In the embodiment, as shown in FIG. 12, the first RTD1 has asymmetrical current-voltage characteristics. Similarly, the second RTD2 also has asymmetrical current-voltage characteristics.

Moreover, as shown in FIG. 13, the first anode A1 is connected to the second cathode K2, and the first cathode K1 is connected to the second anode A2, in the THz device 30 according to the second embodiment.

(Asymmetrical Current-Voltage Characteristics)

Figure 14:
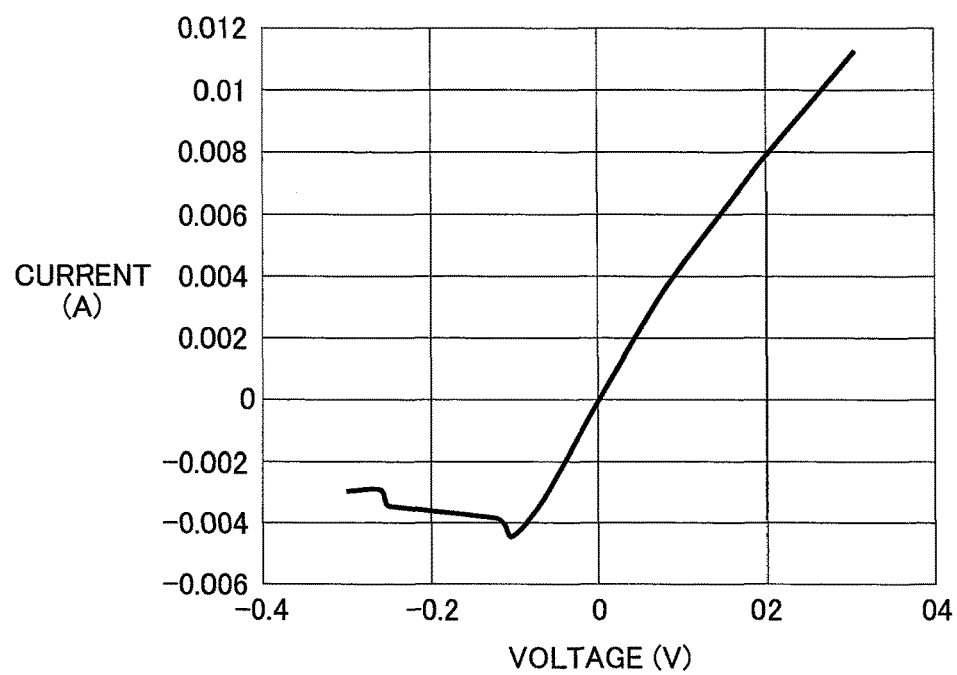
FIG. 14 shows an example of asymmetrical current-voltage characteristics of the RTD1 applicable to the THz device according to a second embodiment.

FIG. 14 shows an enlarged view of an example of asymmetrical current-voltage characteristics of the first RTD1 applicable to the THz device 30 according to the second embodiment, in which the forward voltage value is within a range of −400 mV to +400 mV. Moreover, FIG. 15 shows an enlarged view of an example of asymmetrical current-voltage characteristics of the second RTD2 applicable to the THz device 30 according to the second embodiment, in which the forward voltage value is within a range of −400 mV to +400 mV.

Figure 15:
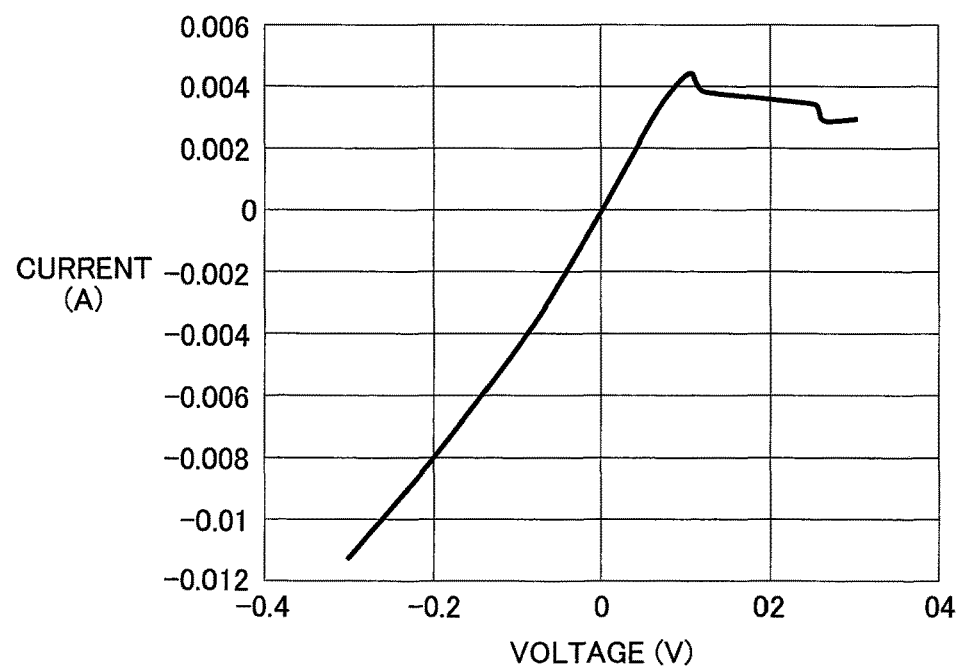
FIG. 15 shows an example of asymmetrical current-voltage characteristics of an RTD2 applicable to the THz device according to the second embodiment.
Figure 16:
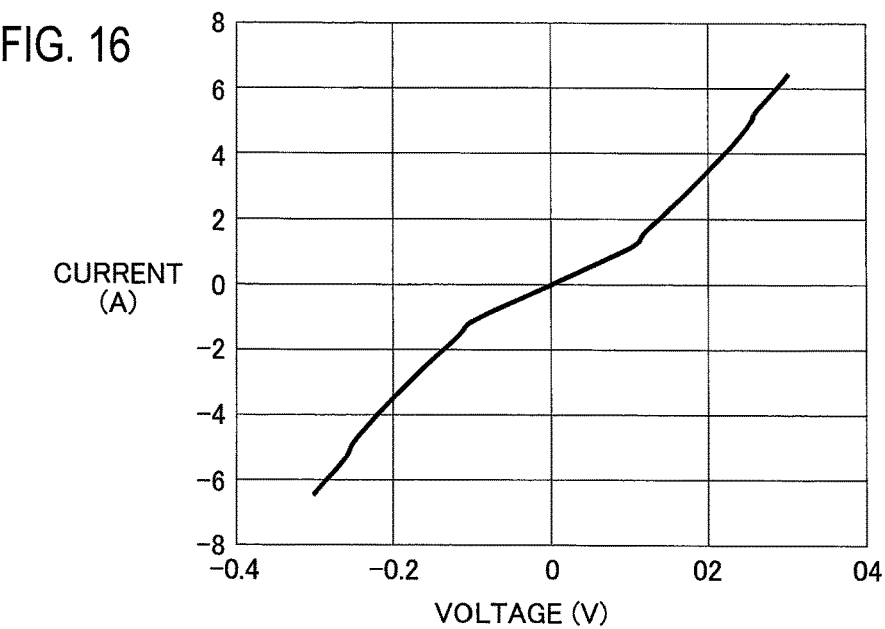
FIG. 16 shows an example of current-voltage characteristics estimated on the basis of a combined resistance of the RTD1 and the RTD2, in the THz device according to the second embodiment.

Moreover, FIG. 16 shows an example of current-voltage characteristics estimated from a combined resistance between the first RTD1 and the second RTD2, on the basis of the characteristics shown in FIGS. 14 and 15, in the THz device 30 according to the second embodiment. According to this calculated result, it is proved that an effect of sufficiently suppressing the parasitic oscillation can be produced by connecting two RTDs in parallel to each other so as to reverse the polarity.

An equivalent circuit as shown in FIG. 13 can be composed by connecting two RTDs having the current-voltage characteristics shown in FIGS. 14 and 15 in parallel to each other so as to reverse the polarity. At this time, it is assumed that RF (THz frequencies) oscillation is tried using a negative resistance region at the minus side of one of the RTDs. If +200 mV is applied, since a voltage of −200 mV is applied to the one of the RTDs, bias is applied to the negative resistance region, and then it becomes a driving voltage. At this time, a voltage of +200 mV is applied to the other of the RTDs, and then it is behaved as a pure resistor.

For example, in the example of the asymmetrical current-voltage characteristics of the first RTD1 (FIG. 14), the first RTD1 is in a pure resistance state if the forward voltage value is in a bias state which is +200 mV, and the first RTD1 is in a negative resistance state if the forward voltage value is in a bias state which is −200 mV. On the other hand, in the example of the asymmetrical current-voltage characteristics of the second RTD2 (FIG. 15), the second RTD2 is in a negative resistance state if the forward voltage value is in a bias state which is +200 mV, and the second RTD2 is in a pure resistance state if the forward voltage value is in a bias state which is −200 mV.

Accordingly, in the THz device 30 according to the second embodiment, since the first RTD1 and the second RTD2 are connected reversely in parallel to each other, if the one of the first RTD1 and the second RTD2 is biased to the negative-resistance oscillation state, the other can be biased to a resistance state.

As clearly from a comparison between the current-voltage characteristics of the first RTD1 shown in FIGS. 12 and 14, and the current-voltage characteristics estimated from the combined resistance shown in FIG. 16, since the first RTD1 and the second RTD2 are connected reversely in parallel to each other, if the first RTD1 is biased to the negative-resistance oscillation state, the second RTD2 can be biased to a resistance state, in the THz device 30 according to the second embodiment. Thus, according to the THz device 30 according to the second embodiment, the parasitic oscillation between the RTD and the external circuit can be suppressed without forming metal wiring.

In the THz device 30 according to the second embodiment, the THz oscillator using the second RTD2 for suppressing the parasitic oscillation with respect to the external circuit can be provided with regard to the device structure for suppressing the parasitic oscillation of the first RTD1.

Such a method is fundamental technology generalizable as a method of suppressing a parasitic oscillation not only in the THz wave bands, but also with respect to RTD and its external circuit. More specifically, it is a method realized by disposing two RTDs, having asymmetrical current-voltage characteristics at plus and minus sides, in parallel to each other so as to reverse the polarity.

The RTD behaves such as a pure resistor, in a voltage region lower than a voltage range which indicates the negative resistance. The matter of reversing the polarity means that the other RTD behaves as a resistor during the one RTD is going to be the negative resistance.

Thus, the device structure for suppressing the parasitic oscillation can be fabricated on the same epitaxial substrate and in the same process, as mentioned below.

In the THz device 30 according to the second embodiment, the number of processes required for metal wiring can be reduced, and thereby also contributing to improve reliability of the device. Moreover, since the same epitaxial substrate is used, there is no need to add a new epitaxial film and add processes therefor. Moreover, such a device structure can be realized only by change of a mask, and thereby it can also contribute to the suppression of a ultimate fabricating cost. Since an inductance of the metal wiring portion can be removed, high-speed modulation characteristics can also be improved.

(Device Structure)

Figure 17:
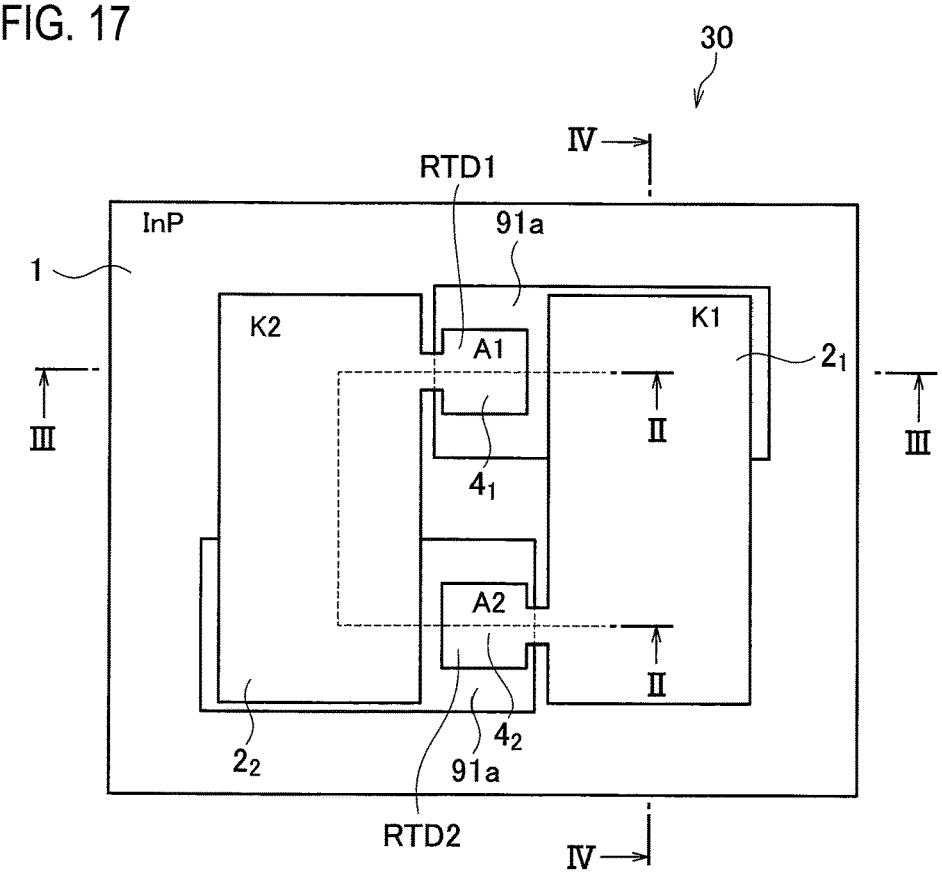
FIG. 17 is a schematic plane configuration diagram showing a wiring structure of the THz device according to the second embodiment.
Figure 18:
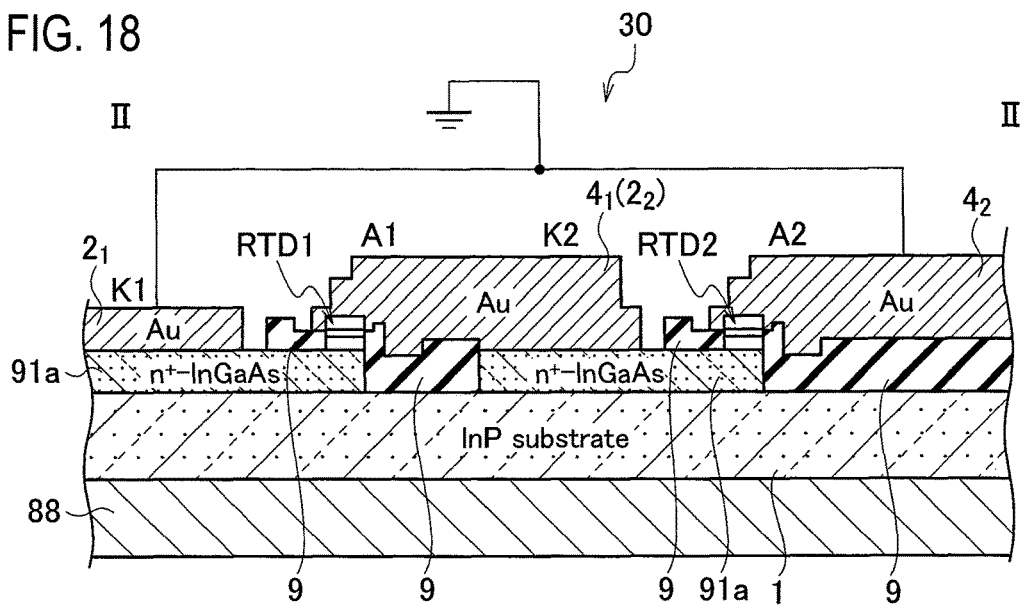
FIG. 18 is a schematic cross-sectional structure diagram taken in the line II-II of FIG. 17.
Figure 19:
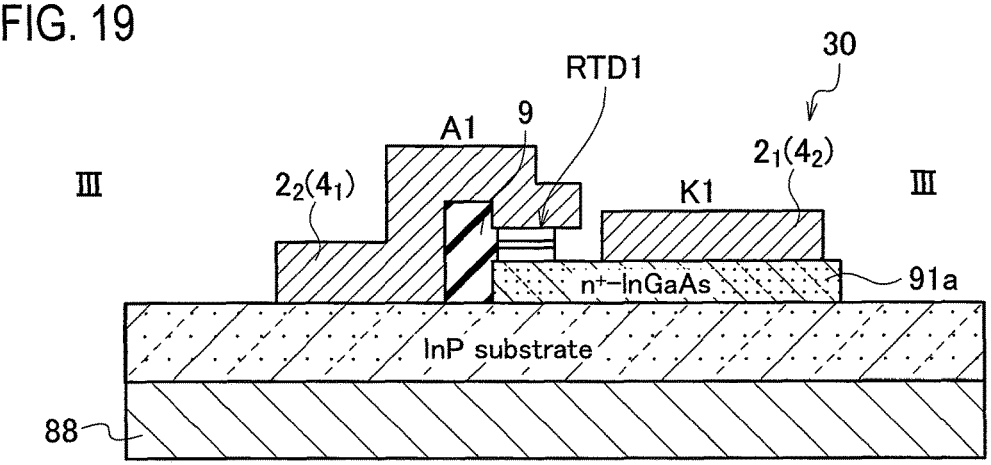
FIG. 19 is a schematic cross-sectional structure diagram taken in the line of FIG. 17.
Figure 20:
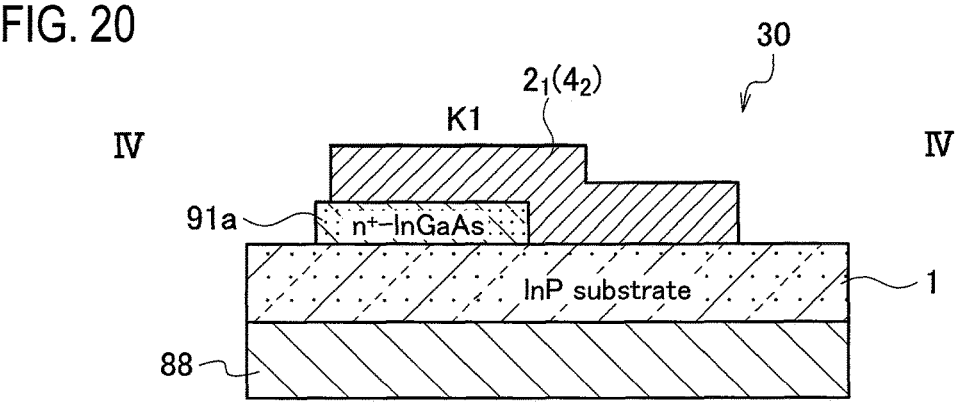
FIG. 20 is a schematic cross-sectional structure diagram taken in the line IV-IV of FIG. 17.

FIG. 17 shows a schematic plane configuration of a wiring structure of the THz device 30 according to the second embodiment, FIG. 18 shows a schematic cross-sectional structure taken in the line II-II of FIG. 17, FIG. 19 shows a schematic cross-sectional structure taken in the line III-III of FIG. 17, and FIG. 20 shows a schematic cross-sectional structure taken in the line IV-IV of FIG. 17.

The THz device 30 according to the second embodiment may include a semiconductor substrate 1, and the first RTD1 and the second RTD2 may be disposed on the semiconductor substrate 1. In the present embodiment, a semi-insulating InP substrate etc. can be applied to the semiconductor substrate 1, for example.

A rear reflector metal layer 88 is disposed on a back side surface of the semiconductor substrate 1 of the THz device 30 according to the second embodiment in the same manner as the THz device 30 according to the first embodiment.

Moreover, the first RTD1 and the second RTD2 may be integrated onto the semiconductor substrate 1, as shown in FIGS. 17-20.

(Integrated THz Oscillation Device)

As shown in FIGS. 17-20, the THz device 30 according to the second embodiment capable of operating as an integrated THz oscillation device includes: a semiconductor substrate 1; a first semiconductor layer 91a disposed on the semiconductor substrate 1; a first cathode region and a second cathode region formed by patterning the first semiconductor layer 91a; a first RTD1 of which a first cathode K1 is connected to the first cathode region, and a first anode A1 is connected to the second cathode region; a second RTD2 of which a second cathode K2 is connected to the second cathode region, and a second anode A2 is connected to the first cathode region; and a rear reflector metal layer 88 disposed on a back side surface of the semiconductor substrate 1 opposite to the first semiconductor layer 91a. In the embodiment, when the first RTD1 is biased to a negative-resistance oscillation state, the second RTD2 is biased to a resistance state; electromagnetic waves emitted from the first RTD1 are reflected on the rear reflector metal layer 88, and have a surface light-emission radiating pattern in a vertical direction with respect to the semiconductor substrate 1.

Moreover, the first RTD1 and the second RTD2 have asymmetrical current-voltage characteristics.

Moreover, as shown in FIGS. 17-20, the THz device 30 according to the second embodiment includes: a first cathode electrode $2_1$ disposed on the first cathode region; a second cathode electrode $2_2$ disposed on the second cathode region; a first anode electrode $4_1$ connected to the first anode A1; and a second anode electrode $4_2$ connected to the second anode A2, wherein the first cathode electrode $2_1$ is commonly connected with the second anode electrode $4_2$, and the second cathode electrode $2_2$ is commonly connected with the first anode electrode $4_1$.

In addition, as shown in FIG. 18, an interlayer insulating film 9 is formed on a place needed to be electrically insulated. The interlayer insulating film 9 can be formed by including an $SiO_2$ film, for example. The interlayer insulating film 9 can be formed by using the CVD method or the spattering technique.

(Integrated THz Detection Device)

The THz device 30 according to the second embodiment capable of operating as an integrated THz detection device includes the configuration similar to the above-mentioned THz oscillation device, wherein when the first RTD1 is biased to a negative-resistance oscillation state, the second RTD2 is biased to a resistance state; wherein electromagnetic waves received from the first RTD1 are reflected on the rear reflector metal layer 88, and have a surface light-receiving pattern in a vertical direction with respect to the semiconductor substrate 1.

(Detailed Structure)

As shown in FIG. 21, a constructional example of the RTD applicable to the THz device according to the first embodiment includes: an GaInAs layer 91a formed on a semiconductor substrate 1 composed including a semi insulating InP substrate, the GaInAs layer 91a highly doped with an n type impurity; a GaInAs layer 92a disposed on the GaInAs layer 91a, the GaInAs layer 92a doped with an n type impurity; a undoped GaInAs layer 93a disposed on the GaInAs layer 92a; an RTD portion composed by including an AlAs layer 94a/GaInAs layer 95/AlAs layer 94b disposed on the GaInAs layer 93a; an undoped GaInAs layer 93b disposed on the AlAs layer 94b; a GaInAs layer 92b disposed on the GaInAs layer 93a, the GaInAs layer 92b doped with an n type impurity; a GaInAs layer 91c disposed on the GaInAs layer 92b, the GaInAs layer 91b highly doped with an n type impurity; a first electrode $4_1$ disposed on the GaInAs layer 91c; and a second electrode $2_1$ disposed on the GaInAs layer 91a.

As shown in FIG. 21, the quantum well structure QW1 of the first RTD1 is formed so that the GaInAs layer 95 is inserted between the AlAs layers 94a and 94b. The quantum well structure QW1 layered in this way is ohmic-connected to the second electrode $2_1$ and the first electrode $4_1$, by intervening the undoped GaInAs layers 93a and 93b used as spacer layers SP11 and SP12, via the n-type GaInAs layers 92a, 92b and the $n^+$ type GaInAs layers 91a, 91b, or 91a, 91b, 91c.

Similarly, as shown in FIG. 21, the quantum well structure QW2 of the second RTD2 is formed so that the GaInAs layer 95 is inserted between the AlAs layers 94a and 94b. The quantum well structure QW2 layered in this way is ohmic-connected to the second electrode $2_1$ and the first electrode $4_1$, by intervening the undoped GaInAs layers 93a and 93b used as spacer layers SP21 and SP22, via the n-type GaInAs layers 92a, 92b and the $n^+$ type GaInAs layers 91a, 91b, or 91a, 91b, 91c.

As shown in FIG. 21, in the THz device 30 according to the second embodiment, the first RTD1 and the second RTD2 respectively include: quantum well layers 95; first spacer layers SP11 (93a) and SP21 (93a) disposed at the cathode K side and second spacer layers SP12 (93b) and SP22 (93b) disposed at the anode A side, via tunnel barrier layers 94a and 94b which respectively sandwich the quantum well layers 95, wherein the thickness of the first spacer layer SP11 and the thickness of the second spacer layer SP12 may be composed so as to be different from each other.

Moreover, the first RTD1 and the second RTD2 may be composed so that the thickness of the first spacer layer SP11 and the thickness of the first spacer layer SP21 are different from each other, in the THz device 30 according to the second embodiment.

Moreover, the first RTD1 and the second RTD2 may be composed so that the thickness of the second spacer layer SP12 and the thickness of the second spacer layer SP22 are different from each other, in the THz device 30 according to the second embodiment.

The first RTD1 and the second RTD2 applicable to the THz device 30 according to the second embodiment have the asymmetrical current-voltage characteristics in the plus and minus sides, by changing the thicknesses of the quantum well structures QW1 and QW2 which develop the resonant tunneling effect, and the thicknesses of the spacer layers (SP11, SP12) and (SP21, SP22) disposed above and below the quantum well structures QW1 and QW2 so as to sandwich the quantum well structures QW1 and QW2. This is caused by the number of carriers injected into the quantum well layer 95 in the quantum well structures QW1 and QW2 being different in a direction of the bias due to the thicknesses of the spacer layers (SP11, SP12) and (SP21, SP22). The introduction of the asymmetry by changing the thicknesses of the spacer layers (SP11, SP12) and (SP21, SP22) can realize the THz device 30 according to the second embodiment.

Moreover, it is preferable that the distance D between the quantum well structures QW1 and QW2 of the first RTD1 and the second RTD2 and the surface of the rear reflector metal layer 88 contacted with the semiconductor substrate 1 is ¼ times as long as the wavelength λ, in the THz device 30 according to the second embodiment. This is for the purpose of obtaining efficiently a satisfactory surface light-emission radiating pattern or surface light-receiving pattern in the vertical direction with respect to the semiconductor substrate 1.

The asymmetrical current-voltage characteristics as shown in FIG. 12 or 14 can be obtained by introducing the asymmetry, e.g., setting the thicknesses of the spacer layers SP11 and SP12 respectively to 20 nm and 2 nm, in the first RTD1 applicable to the THz device 30 according to the second embodiment.

Similarly, the asymmetrical current-voltage characteristics as shown in FIG. 15 can be obtained by introducing the asymmetry, e.g., setting the thicknesses of the spacer layers SP21 and SP22 respectively to 2 nm and 20 nm, in the second RTD2 applicable to the THz device 30 according to the second embodiment.

In the embodiment the thickness of each layer is, for example, as follows:

The thicknesses of the $n^+$ GaInAs layers 91a, 91b, 91c are respectively approximately 400 nm, approximately 15 nm, and approximately 8 nm, for example. The thicknesses of the n type GaInAs layers 92a and 92b are substantially equal to each other, and respectively are approximately 25 nm, for example. The thicknesses of the undoped GaInAs layers 93a and 93b are thicknesses for realizing the above-mentioned asymmetry, for example, and respectively are approximately 2 nm and 20 nm. The thicknesses of the AlAs layers 94a and 94b are equal to each other, and respectively are approximately 1.1 nm, for example. The thickness of the GaInAs layer 95 is approximately 4.5 nm, for example.

In addition, an $SiO_2$ film, an $Si_3N_4$ film, a SiON film, an $HfO_2$ film, an $Al_2O_3$ film, etc., or an insulating film composed by including the aforementioned multilayer films is deposited on the sidewall part of the layered structure shown in FIG. 21. The insulating layer can be formed by CVD or a spattering technique.

Figure 22:
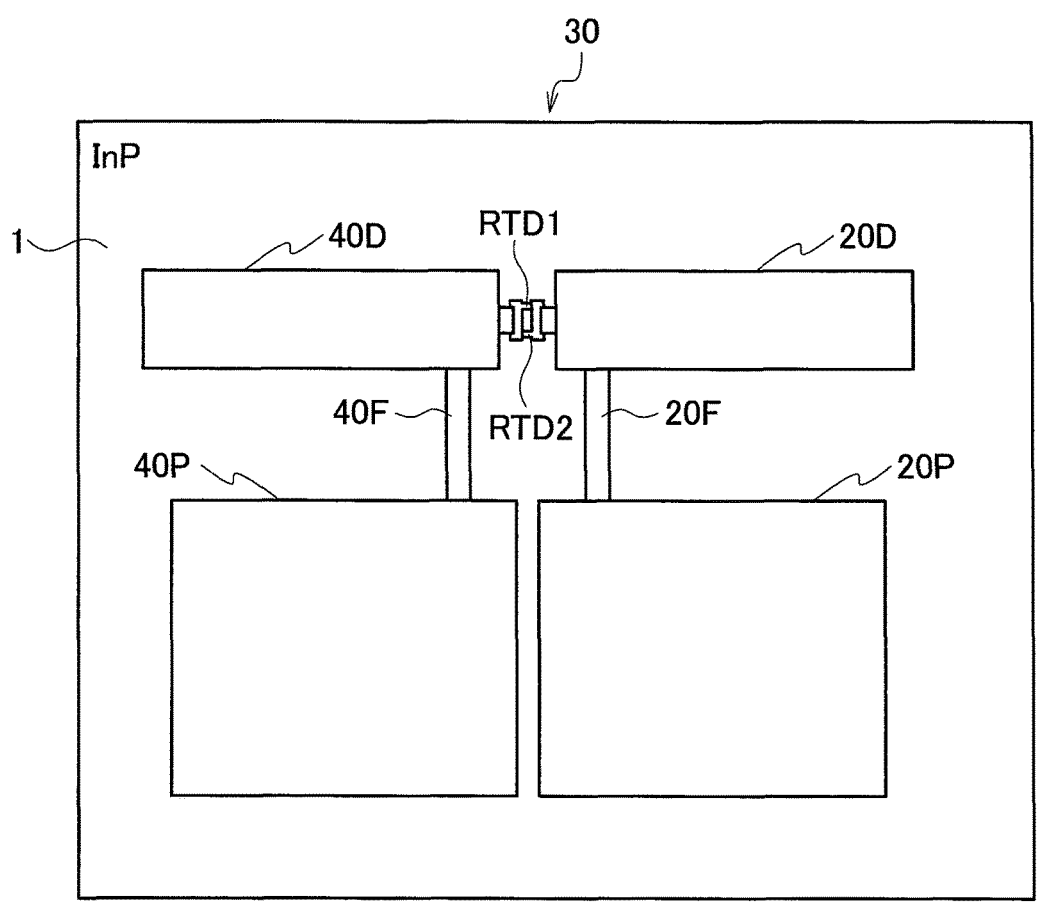
FIG. 22 is a schematic planar pattern configuration diagram showing the THz device according to the second embodiment including a dipole antenna.

FIG. 22 shows a schematic planar pattern configuration of the THz device 30 according to the second embodiment including a dipole antenna.

As shown in FIG. 22, the THz device 30 according to the second embodiment includes dipole antennas 40D and 20D respectively connected to the cathode electrodes $2_2$ and $2_1$.

As shown in FIG. 22, the THz device 30 according to the second embodiment may include: feed lines 40F and 20F respectively connected to the dipole antennas 40D and 20D; and pad electrodes 40P and 20P respectively connected to the feed lines 40F and 20F.

Moreover, the THz device 30 according to the embodiments may include an MIM reflector (not shown) connected between the pad electrodes 40P and 20P.

Due to the layered structure composed by including the metal/insulator/metal of the MIM reflector, the pad electrodes 40P, 20P are short-circuited in terms of high frequencies. Moreover, the MIM reflector produces an effect to reflect high-frequency waves as it is open in terms of direct current.

Each of the dipole antennas 40D and 20D is composed by including a metal layered structure of Au/Pd/Ti, for example, and the Ti layer is a buffer layer for making satisfactorily a contact state with the semiconductor substrate 1 including a semi insulating InP substrate. The thickness of each unit of the dipole antennas 40D and 20D is approximately several 100 nm, for example, a planarized layered structure as shown in FIG. 22 is produced as a whole. Each of the dipole antennas 40D and 20D can be formed by a vacuum evaporation method or a sputtering technique.

(Fabrication Method)

A fabrication method of the THz device according to the second embodiment includes: forming a first semiconductor layer 91a on a semiconductor substrate 1; patterning the first semiconductor layer 91a so as to form a first cathode region and a second cathode region; forming a first RTD1 of which a first cathode K1 is connected to the first cathode region and a first anode A1 is connected to the second cathode region; forming a second RTD2 of which a second cathode K2 is connected to the second cathode region and a second anode A2 is connected to the first cathode region; forming a first cathode electrode $2_1$ on the first cathode region, the first cathode electrode $2_1$ commonly connected with a second anode electrode $4_2$; and forming a second cathode electrode $2_2$ on the second cathode region, the second cathode electrode $2_2$ commonly connected with a first anode electrode $4_1$.

Moreover, the steps of forming the first RTD1 and the second RTD2 include: forming first spacer layers SP11 (93a) and SP21 (93a) on the first semiconductor layer 91a; forming first tunnel barrier layers 94a and 94a respectively on the first spacer layers SP11 (93a) and SP21 (93a); forming quantum well layers 95 and 95 respectively on the first tunnel barrier layers 94a and 94a; forming second tunnel barrier layers 94b and 94b respectively on the quantum well layers 95 and 95; and forming second spacer layers SP12 (93b) and SP22 (93b) respectively on the second tunnel barrier layers 94b and 94b, the thicknesses of the second spacer layers SP12 (93b) and SP22 (93b) being respectively different from the thicknesses of the first spacer layers SP11 (93a) and SP21 (93a).

The structures of the first RTD1 and the second RTD2 applicable to the THz device 30 according to the second embodiment can be formed by the same fabricating process.

FIG. 21 shows a schematic cross-sectional structure of the integrated first RTD1 and second RTD2 portions of the THz device according to the second embodiment, in a schematic cross-sectional structure of the first RTD1 and the second RTD2 fabricated by the same process. Since other configurations are the same as those shown in FIGS. 3A and 3B, the duplicated explanation of each part is omitted.

If the thicknesses of the spacer layers SP11 and SP12 of the first RTD1 is respectively set to 20 nm and 2 nm and the thickness of the spacer layers SP21 and SP22 of the second RTD2 is respectively set to 2 nm and 20 nm; then it is necessary to use selectively step of performing commonly epitaxial growth on both the first RTD1 and the second RTD2 side; step of performing epitaxial growth with respect to only the first RTD1 side by applying a mask on the second RTD2 side, or step of performing epitaxial growth with respect to only the second RTD2 side by applying a mask on the first RTD1 side, in the THz device 30 according to the second embodiment. Other fabricating processed of the respective layers can be formed by the common processes for both the first RTD1 and the second RTD2.

For example, each oscillation frequency observed at a room temperature in the first RTD1 and the second RTD2 fabricated by the same process is approximately 300 GHz.

According to the fabrication method of the THz device 30 according to the second embodiment, since the parasitic oscillation between the RTD and the external circuit can be suppressed without metal wiring, and therefore the fabricating process of the metal wiring becomes unnecessary, the number of the processes can be decreased.

In the THz device 30 according to the second embodiment, although an example of the first tunnel barrier layer/quantum well layer/second tunnel barrier layer has a configuration of AlAs/InAlAs/AlAs is shown, it is not limited to such materials. For example, an example of the first tunnel barrier layer/quantum well layer/second tunnel barrier layer having a configuration of AlGaAs/GaAs/AlGaAs may be suitable therefor. Alternatively, an example of the first tunnel barrier layer/quantum well layer/second tunnel barrier layer having a configuration of AlGaN/GaN/AlGaN may be suitable therefor. Alternatively, an example of the first tunnel barrier layer/quantum well layer/second tunnel barrier layer having a configuration of SiGe/Si/SiGe may be suitable therefor.

The following points are similar also in each configuration: The asymmetrical current-voltage characteristics are realized by disposing the first spacer layer so as to be contacted the first tunnel barrier layer, and disposing the second spacer layer so as to be contacted with the second tunnel barrier layer, and setting the thicknesses of the first spacer layer and the second spacer layer to be different from each other. Then, if the first RTD1 and the second RTD2 having such asymmetrical current-voltage characteristics are connected reversely in parallel to each other, and the one of the first RTD1 and the second RTD2 is biased to the negative-resistance oscillation state, the other is biased to the resistance state.

As explained above, according to the embodiments, there can be provided the THz device which has the surface light-emission radiating pattern or the surface light-receiving pattern; and the fabrication method of such a THz device.

Other Embodiments

As explained above, the THz device according to the embodiments have been described, as a disclosure including associated description and drawings to be construed as illustrative, not restrictive. This disclosure makes clear a variety of alternative embodiments, working examples, and operational techniques for those skilled in the art.

Such being the case, the embodiments described herein cover a variety of embodiments, whether described or not.

INDUSTRIAL APPLICABILITY

The THz device of the embodiments can be applied to THz oscillators, THz detectors, high-frequency resonant circuits, signal amplifiers, etc. on a device basis; and can be applied to wide fields, such as measurement in various fields, e.g., a physical property, an astronomy, a biology, etc. and a security field, other than large-capacity communications and information processing of THz wave imaging devices, sensing devices, high-speed wireless communications devices, etc., on an applicability basis.

What is claimed is:
1. A terahertz device comprising:
a semiconductor substrate;
a first semiconductor layer disposed on the semiconductor substrate;
an active element formed by being laminated on the first semiconductor layer;
a second electrode connected to the first semiconductor layer so as to be connected to one side of a main electrode of the active element, the second electrode disposed on the semiconductor substrate;
a first electrode connected to another side of the main electrode of the active element, the first electrode disposed on the semiconductor substrate so as to be opposite to the second electrode; and
a rear reflector metal layer disposed on aback side surface of the semiconductor substrate opposite to the first semiconductor layer, wherein
the active element forms a resonator between the second electrode and the first electrode, wherein
electromagnetic waves are reflected on the rear reflector metal layer, and electromagnetic waves have a surface light-emission radiating pattern or surface light-receiving pattern in a vertical direction with respect to the semiconductor substrate.

2. The terahertz device according to claim 1, wherein a distance between the active element and a front side surface of the rear reflector metal layer contacted with the semiconductor substrate is ¼ times as long as wavelength λ.

3. The terahertz device according to claim 1, wherein the first electrode and the second electrode comprise a dipole antenna.

4. The terahertz device according to claim 3, further comprising:
a first feed line and a second feed line each which is connected to the dipole antenna; and
a first pad electrode and a second pad electrode respectively connected to the first feed line and the second feed line.

5. The terahertz device according to claim 4, further comprising
an MIM reflector connected between the first pad electrode and the second pad electrode.

6. The terahertz device according to claim 1, further comprising:
a resistance element connected between the first electrode and the second electrode.

7. The terahertz device according to claim 6, wherein the resistance element comprises metallic wiring.

8. The terahertz device according to claim 7, wherein the metallic wiring comprises one selected from the group consisting of Bi, Ni, Ti, and Pt.

9. The terahertz device according to claim 1, wherein the active element is arranged as multichip implementation.

10. The terahertz device according to claim 9, wherein the active element is arranged as cell array implementation.

11. The terahertz device according to claim 1, wherein the active element is one selected from the group consisting of a resonant tunneling diode, a TUNNETT diode, an IMPATT diode, a GaAs based field-effect transistor, a GaN based FET, a high electron mobility transistor, and a hetero-junction bipolar transistor.

12. A terahertz device comprising:
a semiconductor substrate;
a first semiconductor layer disposed on the semiconductor substrate;
a first cathode region and a second cathode region formed by patterning the first semiconductor layer;
a first resonant tunneling diode of which a first cathode is connected to the first cathode region, and a first anode is connected to the second cathode region;
a second resonant tunneling diode of which a second cathode is connected to the second cathode region, and a second anode is connected to the first cathode region; and a rear reflector metal layer disposed on aback side surface of the semiconductor substrate opposite to the first semiconductor layer, wherein when the first resonant tunneling diode is biased to a negative-resistance oscillation state, the second resonant tunneling diode is biased to a resistance state, wherein electromagnetic waves are reflected on the rear reflector metal layer, and electromagnetic waves have a surface light-emission radiating pattern or surface light-receiving pattern in a vertical direction with respect to the semiconductor substrate.

13. The terahertz device according to claim 12, further comprising:
a first cathode electrode disposed on the first cathode region;
a second cathode electrode disposed on the second cathode region;
a first anode electrode connected to the first anode; and
a second anode electrode connected to the second anode, wherein
the first cathode electrode is commonly connected with the second anode electrode, and the second cathode electrode is commonly connected with the first anode electrode.

14. The terahertz device according to claim 12, wherein the first resonant tunneling diode and the second resonant tunneling diode respectively comprise:
quantum well layers;
second spacer layers disposed at an anode side via tunnel barrier layers respectively sandwiching the quantum well layers; and
first spacer layers disposed at a cathode side, wherein
a thickness of the first spacer layer and a thickness of the second spacer layer is different from each other.

15. The terahertz device according to claim 12, wherein a thickness of the first spacer layer in the first resonant tunneling diode and a thickness of the first spacer layer in the second resonant tunneling diode are different from each other.

16. The terahertz device according to claim 12, wherein a thickness of the second spacer layer in the first resonant tunneling diode and a thickness of the second spacer layer in the second resonant tunneling diode are different from each other.

17. The terahertz device according to claim 12, further comprising
dipole antennas respectively connected to the first cathode and the second cathode.

18. The terahertz device according to claim 17, further comprising:
feed lines respectively connected to the dipole antennas; and
pad electrodes respectively connected to the feed lines.

19. The terahertz device according to claim 12, further comprising
an MIM reflector connected between the first cathode and the second cathode.

20. A fabrication method of a terahertz device comprising:
forming a first semiconductor layer on a semiconductor substrate;
patterning the first semiconductor layer so as to form a first cathode region and a second cathode region;
forming a first resonant tunneling diode of which a first cathode is connected to the first cathode region and a first anode is connected to the second cathode region;
forming a second resonant tunneling diode of which a second cathode is connected to the second cathode region and a second anode is connected to the first cathode region;
forming a first cathode electrode on the first cathode region, the first cathode electrode commonly connected with a second anode electrode;
forming a second cathode electrode on the second cathode region, the second cathode electrode commonly connected with a first anode electrode; and
forming a rear reflector metal layer on a back side surface of the semiconductor substrate opposite to the first semiconductor layer.

21. The fabrication method of a terahertz device according to claim 20, wherein the steps of forming the first resonant tunneling diode and the second resonant tunneling diode comprise:
forming first spacer layers on the first semiconductor layer;
forming first tunnel barrier layers respectively on the first spacer layers;
forming quantum well layers respectively on the first tunnel barrier layers;
forming second tunnel barrier layers respectively on the quantum well layers; and
forming second spacer layers respectively on the second tunnel barrier layer, the thicknesses second spacer layers being respectively different from the thicknesses of the first spacer layers.

* * * * *